US006943020B2

(12) United States Patent
Ni et al.

(10) Patent No.: US 6,943,020 B2
(45) Date of Patent: *Sep. 13, 2005

(54) DEATH DOMAIN CONTAINING RECEPTOR-4 ANTIBODIES

(75) Inventors: Jian Ni, Rockville, MD (US); Craig A. Rosen, Laytonsville, MD (US); James G. Pan, Ypsilanti, MI (US); Reiner L. Gentz, Silver Spring, MD (US); Vishva M. Dixit, Los Altos Hills, CA (US)

(73) Assignees: Human Genome Sciences, Inc., Rockville, MD (US); The Regents of the University of Michigan, Ann Arbor, MI (US)

( * ) Notice: Subject to any disclaimer, the term of this patent is extended or adjusted under 35 U.S.C. 154(b) by 533 days.

This patent is subject to a terminal disclaimer.

(21) Appl. No.: 10/226,296

(22) Filed: Aug. 23, 2002

(65) Prior Publication Data

US 2003/0036168 A1 Feb. 20, 2003

Related U.S. Application Data

(60) Continuation of application No. 09/448,868, filed on Nov. 24, 1999, now Pat. No. 6,461,823, which is a division of application No. 09/013,895, filed on Jan. 27, 1998, now Pat. No. 6,342,363.
(60) Provisional application No. 60/037,829, filed on Feb. 5, 1997, and provisional application No. 60/035,722, filed on Jan. 28, 1997.

(51) Int. Cl.$^7$ ...................... C07K 16/28; C07K 14/705; C12N 5/12
(52) U.S. Cl. ...................... 435/328; 435/326; 435/334; 530/350; 530/387.1; 530/387.3; 530/388.1; 530/388.22; 530/389.1; 530/391.1; 530/391.3; 536/23.5
(58) Field of Search .............................. 530/350, 387.1, 530/387.3, 387.7, 387.9, 388.1, 388.22, 388.8, 389.1, 389.7, 391.1, 391.3; 536/23.5; 435/326, 328, 334, 330, 7.1, 7.92

(56) References Cited

U.S. PATENT DOCUMENTS

| 5,763,223 | A | 6/1998 | Wiley et al. |
| 6,342,363 | B1 | 1/2002 | Ni et al. |
| 6,433,147 | B1 | 8/2002 | Ni et al. |
| 6,461,823 | B1 | 10/2002 | Ni et al. |
| 2003/0036168 | A1 | 2/2003 | Ni et al. |
| 2003/0108516 | A1 | 6/2003 | Ni et al. |

FOREIGN PATENT DOCUMENTS

| EP | 0 857 782 A2 | 8/1998 |
| WO | WO 97/01633 | 1/1997 |
| WO | WO 98/32856 A1 | 7/1998 |
| WO | WO 99/02653 | 1/1999 |
| WO | WO 99/11791 | 3/1999 |
| WO | WO 99/37684 | 7/1999 |

OTHER PUBLICATIONS

Chantry, D., "Tumour necrosis factor antagonists," *Emerging Drugs* 4:5–13, Ashley Publications Ltd (1999).

Delgado, C., et al., "Quantitative analysis of polyethylene glycol (PEG) in PEG–modified proteins/cytokines by aqueous two–phase systems," *J. Biochem. Biophys. Methods* 29:237–250, Elsevier Science (1994).

Kim, K., et al., "Molecular determinants of response to TRAIL combined with chemotherapy in killing of normal cancer cells," *Proceedings of the American Association for Cancer Research Annual Meeting* 40:486, 90$^{th}$ Annual Meeting of the American Association for Cancer Research (Apr. 1999).

Marsters, S.A., et al., "Control of Apoptosis Signaling by Apo2 Ligand," *Recent Progress in Hormone Research* 54:225–234, The Endocrine Society (1999).

International Search Report for International Application No. PCT/US 98/01464, European Patent Office, Netherlands, mailed on Jun. 17, 1998.

Supplementary Partial European Search Report for European Application No. EP 00 932061, European Patent Office, Netherlands, completed on Aug. 23, 2004.

Chinnaiyan, A.M., et al., "Signal Transduction by DR3, a Death Domain–Containing Receptor Related to TNFR–1 and CD95," *Science* 274:990–992, American Association for the Advancement of Science (Nov. 1996).

EMBL Database, Accession No. AA100865, Hillier, L., et al., European Molecular Biology Laboratory (Oct. 30, 1996).

Goodman, J.W., "Immunogens & Antigens," in *Basic & Clinical Immunology*, Stites, D.P., et al., eds., Appleton & Lange, Norwalk, CT, pp. 50–57 (1988).

Lerner, R.A., "Antibodies of Predetermined Specificity in Biology and Medicine," *Adv. Immunol.* 36:1–44, Academic Press (1984).

NCBI Entrez, GenBank Report, Accession No. AA102383, Hillier, L., et al., National Center for Biotechnology Information (Oct. 28, 1996).

NCBI Entrez, GenBank Report, Accession No. W65310, Hillier, L., et al., National Center for Biotechnology Information (Oct. 15, 1996).

(Continued)

Primary Examiner—Lorraine Spector
Assistant Examiner—Claire M. Kaufman
(74) Attorney, Agent, or Firm—Sterne, Kessler, Goldstein & Fox P.L.L.C.

(57) ABSTRACT

The present invention relates to novel Death Domain Containing Receptor-4 (DR4) proteins which are members of the tumor necrosis factor (TNF) receptor family. In particular, isolated nucleic acid molecules are provided encoding the human DR4 proteins. DR4 polypeptides are also provided as are vectors, host cells and recombinant methods for producing the same. The invention further relates to screening methods for identifying agonists and antagonists of DR4 activity.

52 Claims, 10 Drawing Sheets

OTHER PUBLICATIONS

NCBI Entrez, GenBank Report, Accession No. AA102745, Hillier, L., et al., National Center for Biotechnology Information (Oct. 28, 1996).

NCBI Entrez, GenBank Report, Accession No. AA102746, Hillier, L., et al., National Center for Biotechnology Information (Oct. 28, 1996).

NCBI Entrez, GenBank Report, Accession No. AA150849, Hillier, L., et al., National Center for Biotechnology Information (Dec. 10, 1996).

NCBI Entrez, GenBank Report, Accession No. AA639619, Strausberg, R., National Center for Biotechnology Information (Oct. 23, 1997).

Pan, G., et al., "The Receptor for the Cytotoxic Ligand TRAIL," *Science* 276:111–113, American Association for the Advancement of Science (1997).

Ruf, M., and Kössel, H., "Structure and Expression of the Gene Coding for the α–Subunit of DNA–Dependent RNA Polymerase from the Chloroplast Genome of *Zea Mays*," *Nucl. Acids Res.* 16:5741–5754, Oxford University Press (1988).

Strader, C.D., et al., "Structural basis of β–adrenergic receptor function," *FASEB J.* 3:1825–1832, Federatiion of American Societies for Experimental Biology (1989).

Pending Non–Provisional U.S. Appl. No. 10/175,902, Ni et al., filed Jun. 21, 2002.

Pending Non–Provisional U.S. Appl. No. 10/226,318, Ni et al., filed Aug. 23, 2002.

Walczak, H., et al., "TRAIL–R2: a novel apoptosis–mediating receptor for TRAIL," *EMBO J.* 16:5386–5397, Oxford University Press (1997).

```
              10                    30                    50
TTCGGGCACGAGGGCAGGATGGCGCCACCACCAGCTAGAGTACATCTAGGTGCGTTCCTG
                 M   A   P   P   P   A   R   V   H   L   G   A   F   L
              70                    90                   110
GCAGTGACTCCGAATCCCGGGAGCGCAGCGAGTGGGACAGAGGCAGCCGCGGCCACACCC
 A   V   T   P   N   P   G   S   A   S   G   T   E   A   A   A   A   T   P
             130                   150                   170
AGCAAAGTGTGGGGCTCTTCCGCGGGGAGGATTGAACCACGAGGCGGGGGCCGAGGAGCG
 S   K   V   W   G   S   S   A   G   R   I   E   P   R   G   G   G   R   G   A
             190                   210                   230
CTCCCTACCTCCATGGGACAGCACGGACCCAGTGCCCGGGCCCGGGCAGGGCGCGCCCCA
 L   P   T   S   M   G   Q   H   G   P   S   A   R   A   R   A   G   R   A   P
             250                   270                   290
GGACCCAGGCCGGCGCGGGAAGCCAGCCCTCGGCTCCGGGTCCACAAGACCTTCAAGTTT
 G   P   R   P   A   R   E   A   S   P   R   L   R   V   H   K   T   F   K   F
             310                   330                   350
GTCGTCGTCGGGGTCCTGCTGCAGGTCGTACCTAGCTCAGCTGCAACCATCAAACTTCAT
 V   V   V   G   V   L   L   Q   V   V   P   S   S   A   A   T   I   K   L   H
             370                   390                   410
GATCAATCAATTGGCACACAGCAATGGGAACATAGCCCTTTGGGAGAGTTGTGTCCACCA
 D   Q   S   I   G   T   Q   Q   W   E   H   S   P   L   G   E   L   C   P   P
             430                   450                   470
GGATCTCATAGATCAGAACGTCCTGGAGCCTGTAACCGGTGCACAGAGGGTGTGGGTTAC
 G   S   H   R   S   E   R   P   G   A   C   N   R   C   T   E   G   V   G   Y
             490                   510                   530
ACCAATGCTTCCAACAATTTGTTTGCTTGCCTCCCATGTACAGCTTGTAAATCAGATGAA
 T   N   A   S   N   N   L   F   A   C   L   P   C   T   A   C   K   S   D   E
             550                   570                   590
GAAGAGAGAAGTCCCTGCACCACGACCAGGAACACAGCATGTCAGTGCAAACCAGGAACT
 E   E   R   S   P   C   T   T   T   R   N   T   A   C   Q   C   K   P   G   T
             610                   630                   650
TTCCGGAATGACAATTCTGCTGAGATGTGCCGGAAGTGCAGCACAGGGTGCCCCAGAGGG
 F   R   N   D   N   S   A   E   M   C   R   K   C   S   T   G   C   P   R   G
             670                   690                   710
ATGGTCAAGGTCAAGGATTGTACGCCCTGGAGTGACATCGAGTGTGTCCACAAAGAATCA
 M   V   K   V   K   D   C   T   P   W   S   D   I   E   C   V   H   K   E   S
```

FIG.1A

```
     730              750              770
GGCAATGGACATAATATATGGGTGATTTTGGTTGTGACTTTGGTTGTTCCGTTGCTGTTG
 G  N  G  H  N  I  W  V  I  L  V  V  T  L  V  V  P  L  L  L
                   ****************************************
     790              810              830
GTGGCTGTGCTGATTGTCTGTTGTTGCATCGGCTCAGGTTGTGGAGGGGACCCCAAGTGC
 V  A  V  L  I  V  C  C  I  G  S  G  C  G  G  D  P  K  C
*******************************************
     850              870              890
ATGGACAGGGTGTGTTTCTGGCGCTTGGGTCTCCTACGAGGGCCTGGGGCTGAGGACAAT
 M  D  R  V  C  F  W  R  L  G  L  L  R  G  P  G  A  E  D  N
     910              930              950
GCTCACAACGAGATTCTGAGCAACGCAGACTCGCTGTCCACTTTCGTCTCTGAGCAGCAA
 A  H  N  E  I  L  S  N  A  D  S  L  S  T  F  V  S  E  Q  Q
     970              990              1010
ATGGAAAGCCAGGAGCCGGCAGATTTGACAGGTGTCACTGTACAGTCCCCAGGGGAGGCA
 M  E  S  Q  E  P  A  E  L  T  G  V  T  V  Q  S  P  G  E  A
     1030             1050             1070
CAGTGTCTGCTGGGACCGGCAGAAGCTGAAGGGTCTCAGAGGAGGAGGCTGCTGGTTCCA
 Q  C  L  L  G  P  A  E  A  E  G  S  Q  R  R  R  L  L  V  P
     1090             1110             1130
GCAAATGGTGCTGACCCCACTGAGACTCTGATGCTGTTCTTTGACAAGTTTGCAAACATC
 A  N  G  A  D  P  T  E  T  L  M  L  F  F  D  K  F  A  N  I
     1150             1170             1190
GTGCCCTTTGACTCCTGGGACCAGCTCATGAGGCAGCTGGACCTCACGAAAAATGAGATC
 V  P  F  D  *S  W  D  Q  L  M  R  Q  L  D  L  T  K  N  E  I*
     1210             1230             1250
GATGTGGTCAGAGCTGGTACAGCAGGCCCAGGGGATGCCTTGTATGCAATGCTGATGAAA
 *D  V  V  R  A  G  T  A  G  P  G  D  A  L  Y  A  M  L  M  K*
     1270             1290             1310
TGGGTCAACAAAACTGGACGGAACGCCTCGATCCACACCCTGCTGGATGCCTTGGAGAGG
 *W  V  N  K  T  G  R  N  A  S  I  H  T  L  L  D  A  L  E  R*
     1330             1350             1370
ATGGAAGAGAGACATGCAAAAGAGAAGATTCAGGACCTCTTGGTGGACTCTGGAAAGTTC
 *M  E  E  R  H  A  K  E  K  I  Q*  D  L  L  V  D  S  G  K  F
```

FIG. 1B

```
                1390              1410              1430
ATCTACTTAGAAGATGGCACAGGCTCTGCCGTGTCCTTGGAGTGAAAGACTCTTTTTACC
  I  Y  L  E  D  G  T  G  S  A  V  S  L  E
                1450              1470              1490
AGAGGTTTCCTCTTAGGTGTTAGGAGTTAATACATATTAGGTTTTTTTTTTTTTTTAACAT
                1510              1530              1550
GTATACAAAGTAAATTCTTAGCCACGTGTATTGGCTCCTGCCTGTAATCCCATCACTTTG
                1570              1590              1610
GGAGGCTGACGCCGGTGGATCCACTTGAGGTCCGAAGTTCCAAGACCAGCCCTGAACCAA
                1630              1650              1670
CATCGTGGAAATGCCCGTCTTTTACAAAAAAATACCAAAAATTCAACTGGAATGTGCATG
                1690              1710              1730
GTGTGTGCCATCATTTCCTCGGCTAACTACGGGAGGTCTGAGGCCAGGAGAATCCACTTG
                1750              1770              1790
AACCCCACGAAGGACAGTGTAGACTGCAGATTGCACCACTGCACTCCCAGCCTGGGAACA
                1810              1830              1850
CAGAGCAAGACTCTGTCTCAAGATAAAATAAAATAAACTTGAAAGAATTATTGCCCGACT
                1870              1890              1910
GAGGCTCACATGCCAAAGGAAAATCTGGTTCTCCCCTGAGCTGGCCTCCGTGTGTTTCCT
                1930              1950              1970
TATCATGGTGGTCAATTGGAGGTGTTAATTTGAATGGATTAAGGAACACCTAGAACACTG
                1990              2010              2030
GTAAGGCATTATTTCTGGGACATTATTTCTGGGCATGTCTTCGAGGGTGTTTCCAGAGGG
                2050              2070              2090
GATTGGCATGCGATCGGGTGGACTGAGTGGAAAAGACCTACCCTTAATTTGGGGGGGCAC
                2110              2130              2150
CGTCCGACAGACTGGGGAGCAAGATAGAAGAAAACAAAAAAAAAAAAAAAA
```

HTOIY07R

```
  1  GGCANAGGTN CGTACCTAGC TCACCTGCAA CCATCAAACT TNATGATCAA
 51  TCAATTGGCA CACAGCAATG GGAAACATAG CCCTTTGGAA GANTTGTNTC
101  CACCAGGATC TCATAGATCA AAACATCCTG GGAGCCTGTT AACCGGTGCC
151  CCAAAGGNTG GTCAAGGTCA AGGAATTGTT NCGCCCTGGA AGTGAACATC
201  GAGTGTNTCC ACAAAGGATT CAGGCAATGG GACATAAATA TATGGGTGAA
251  TTTTGGTTGT GAACTTTGGT TGNTCCCGTT GNTGTTGNTG GCTGTGCTGA
301  TTGTTTGTTG TTGCATCGGC TTCAGGTTNT GGAGGGGGAC CCAAGTGCAT
351  GGACAGGGTG TGTTTCTGGG GTTTGGGTCT CTTAGAGGGC NTGGGTTANG
401  GCANGTTCAC AAGGGTTTTA GCAANG
```

HTXEY80R

```
  1  TGGGGCTGAG GACAATGCTG ACNACGAGAT TCTGAGCAAC GCAGNACTNG
 51  CTGTCCACTT TCGTCTNTGN GCAGCAAATG GAAAGCCAGG AGCCGGCAGA
101  TTTGACAGGT GTCACTGTAC AGTCCCCAGG GGAGGCACAG TGTCTGCTGG
151  TGAGTTGGGG ACAGGCCCTT GCAAGACCTT GTGAGGCAGG GGGTGAAGGC
201  CATGNCTCGG CTTCNNNTGG TCAAAGGGGA AGTGGAGCCT GAGGGAGATG
251  GGACTTNAGG GGGACGGNGC TGCGTGGGGA AAAAGCAGCC ACCNTTTGAC
301  AAGGGGGACA GGCATTTTTN CAAATGTGTG CTTNTTGGT
```

FIG.4

SEQUENCE LISTING (1) GENERAL INFORMATION:

(iii) NUMBER OF SEQUENCES: 12

(2) INFORMATION FOR SEQ ID NO: 1:

(i) SEQUENCE CHARACTERISTICS:
      (A) LENGTH: 2152 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 19..1422

(xi) SEQUENCE DESCRIPTION: SEQ ID NO: 1:

```
TTCGGGCACG AGGGCAGG ATG GCG CCA CCA CCA GCT AGA GTA CAT CTA GGT         51
                    Met Ala Pro Pro Pro Ala Arg Val His Leu Gly
                     1               5                      10

GCG TTC CTG GCA GTG ACT CCG AAT CCC GGG AGC GCA GCG AGT GGG ACA         99
Ala Phe Leu Ala Val Thr Pro Asn Pro Gly Ser Ala Ala Ser Gly Thr
             15                  20                  25

GAG GCA GCC GCG GCC ACA CCC AGC AAA GTG TGG GGC TCT TCC GCG GGG        147
Glu Ala Ala Ala Ala Thr Pro Ser Lys Val Trp Gly Ser Ser Ala Gly
         30                  35                  40

AGG ATT GAA CCA CGA GGC GGG GGC CGA GGA GCG CTC CCT ACC TCC ATG        195
Arg Ile Glu Pro Arg Gly Gly Gly Arg Gly Ala Leu Pro Thr Ser Met
     45                  50                  55

GGA CAG CAC GGA CCC AGT GCC CGG GCC CGG GCA GGG CGC GCC CCA GGA        243
Gly Gln His Gly Pro Ser Ala Arg Ala Arg Ala Gly Arg Ala Pro Gly
 60                  65                  70                  75

CCC AGG CCG GCG CGG GAA GCC AGC CCT CGG CTC CGG GTC CAC AAG ACC        291
Pro Arg Pro Ala Arg Glu Ala Ser Pro Arg Leu Arg Val His Lys Thr
                 80                  85                  90

TTC AAG TTT GTC GTC GTC GGG GTC CTG CTG CAG GTC GTA CCT AGC TCA        339
Phe Lys Phe Val Val Val Gly Val Leu Leu Gln Val Val Pro Ser Ser
```

|  |  |
|---|---|
| GCT GCA ACC ATC AAA CTT CAT GAT CAA TCA ATT GGC ACA CAG CAA TGG<br>Ala Ala Thr Ile Lys Leu His Asp Gln Ser Ile Gly Thr Gln Gln Trp<br>          110                    115                    120 | 387 |
| GAA CAT AGC CCT TTG GGA GAG TTG TGT CCA CCA GGA TCT CAT AGA TCA<br>Glu His Ser Pro Leu Gly Glu Leu Cys Pro Pro Gly Ser His Arg Ser<br>    125                    130                    135 | 435 |
| GAA CGT CCT GGA GCC TGT AAC CGG TGC ACA GAG GGT GTG GGT TAC ACC<br>Glu Arg Pro Gly Ala Cys Asn Arg Cys Thr Glu Gly Val Gly Tyr Thr<br>140                    145                    150                    155 | 483 |
| AAT GCT TCC AAC AAT TTG TTT GCT TGC CTC CCA TGT ACA GCT TGT AAA<br>Asn Ala Ser Asn Asn Leu Phe Ala Cys Leu Pro Cys Thr Ala Cys Lys<br>                    160                    165                    170 | 531 |
| TCA GAT GAA GAA GAG AGA AGT CCC TGC ACC ACG ACC AGG AAC ACA GCA<br>Ser Asp Glu Glu Glu Arg Ser Pro Cys Thr Thr Thr Arg Asn Thr Ala<br>    175                    180                    185 | 579 |
| TGT CAG TGC AAA CCA GGA ACT TTC CGG AAT GAC AAT TCT GCT GAG ATG<br>Cys Gln Cys Lys Pro Gly Thr Phe Arg Asn Asp Asn Ser Ala Glu Met<br>190                    195                    200 | 627 |
| TGC CGG AAG TGC AGC ACA GGG TGC CCC AGA GGG ATG GTC AAG GTC AAG<br>Cys Arg Lys Cys Ser Thr Gly Cys Pro Arg Gly Met Val Lys Val Lys<br>    205                    210                    215 | 675 |
| GAT TGT ACG CCC TGG AGT GAC ATC GAG TGT GTC CAC AAA GAA TCA GGC<br>Asp Cys Thr Pro Trp Ser Asp Ile Glu Cys Val His Lys Glu Ser Gly<br>220                    225                    230                    235 | 723 |
| AAT GGA CAT AAT ATA TGG GTG ATT TTG GTT GTG ACT TTG GTT GTT CCG<br>Asn Gly His Asn Ile Trp Val Ile Leu Val Val Thr Leu Val Val Pro<br>                    240                    245                    250 | 771 |
| TTG CTG TTG GTG GCT GTG CTG ATT GTC TGT TGT TGC ATC GGC TCA GGT<br>Leu Leu Leu Val Ala Val Leu Ile Val Cys Cys Cys Ile Gly Ser Gly<br>    255                    260                    265 | 819 |
| TGT GGA GGG GAC CCC AAG TGC ATG GAC AGG GTG TGT TTC TGG CGC TTG<br>Cys Gly Gly Asp Pro Lys Cys Met Asp Arg Val Cys Phe Trp Arg Leu<br>270                    275                    280 | 867 |
| GGT CTC CTA CGA GGG CCT GGG GCT GAG GAC AAT GCT CAC AAC GAG ATT<br>Gly Leu Leu Arg Gly Pro Gly Ala Glu Asp Asn Ala His Asn Glu Ile<br>    285                    290                    295 | 915 |
| CTG AGC AAC GCA GAC TCG CTG TCC ACT TTC GTC TCT GAG CAG CAA ATG<br>Leu Ser Asn Ala Asp Ser Leu Ser Thr Phe Val Ser Glu Gln Gln Met<br>300                    305                    310                    315 | 963 |
| GAA AGC CAG GAG CCG GCA GAT TTG ACA GGT GTC ACT GTA CAG TCC CCA<br>Glu Ser Gln Glu Pro Ala Asp Leu Thr Gly Val Thr Val Gln Ser Pro<br>                    320                    325                    330 | 1011 |
| GGG GAG GCA CAG TGT CTG CTG GGA CCG GCA GAA GCT GAA GGG TCT CAG<br>Gly Glu Ala Gln Cys Leu Leu Gly Pro Ala Glu Ala Glu Gly Ser Gln<br>    335                    340                    345 | 1059 |
| AGG AGG AGG CTG CTG GTT CCA GCA AAT GGT GCT GAC CCC ACT GAG ACT<br>Arg Arg Arg Leu Leu Val Pro Ala Asn Gly Ala Asp Pro Thr Glu Thr<br>350                    355                    360 | 1107 |
| CTG ATG CTG TTC TTT GAC AAG TTT GCA AAC ATC GTG CCC TTT GAC TCC<br>Leu Met Leu Phe Phe Asp Lys Phe Ala Asn Ile Val Pro Phe Asp Ser<br>    365                    370                    375 | 1155 |
| TGG GAC CAG CTC ATG AGG CAG CTG GAC CTC ACG AAA AAT GAG ATC GAT<br>Trp Asp Gln Leu Met Arg Gln Leu Asp Leu Thr Lys Asn Glu Ile Asp<br>380                    385                    390                    395 | 1203 |
| GTG GTC AGA GCT GGT ACA GCA GGC CCA GGG GAT GCC TTG TAT GCA ATG<br>Val Val Arg Ala Gly Thr Ala Gly Pro Gly Asp Ala Leu Tyr Ala Met<br>                    400                    405                    410 | 1251 |
| CTG ATG AAA TGG GTC AAC AAA ACT GGA CGG AAC GCC TCG ATC CAC ACC | 1299 |

```
Leu Met Lys Trp Val Asn Lys Thr Gly Arg Asn Ala Ser Ile His Thr
            415                 420                 425

CTG CTG GAT GCC TTG GAG AGG ATG GAA GAG AGA CAT GCA AAA GAG AAG    1347
Leu Leu Asp Ala Leu Glu Arg Met Glu Glu Arg His Ala Lys Glu Lys
            430                 435                 440

ATT CAG GAC CTC TTG GTG GAC TCT GGA AAG TTC ATC TAC TTA GAA GAT    1395
Ile Gln Asp Leu Leu Val Asp Ser Gly Lys Phe Ile Tyr Leu Glu Asp
            445                 450                 455

GGC ACA GGC TCT GCC GTG TCC TTG GAG TGAAAGACTC TTTTTACCAG           1442
Gly Thr Gly Ser Ala Val Ser Leu Glu
460                 465

AGGTTTCCTC TTAGGTGTTA GGAGTTAATA CATATTAGGT TTTTTTTTTT TTTAACATGT   1502

ATACAAAGTA AATTCTTAGC CACGTGTATT GGCTCCTGCC TGTAATCCCA TCACTTTGGG   1562

AGGCTGACGC CGGTGGATCC ACTTGAGGTC CGAAGTTCCA AGACCAGCCC TGAACCAACA   1622

TCGTGGAAAT GCCCGTCTTT TACAAAAAAA TACCAAAAAT TCAACTGGAA TGTGCATGGT   1682

GTGTGCCATC ATTTCCTCGG CTAACTACGG GAGGTCTGAG GCCAGGAGAA TCCACTTGAA   1742

CCCCACGAAG GACAGTGTAG ACTGCAGATT GCACCACTGC ACTCCCAGCC TGGGAACACA   1802

GAGCAAGACT CTGTCTCAAG ATAAAATAAA ATAAACTTGA AGAATTATT GCCCGACTGA   1862

GGCTCACATG CCAAAGGAAA ATCTGGTTCT CCCCTGAGCT GGCCTCCGTG TGTTTCCTTA   1922

TCATGGTGGT CAATTGGAGG TGTTAATTTG AATGGATTAA GGAACACCTA GAACACTGGT   1982

AAGGCATTAT TTCTGGGACA TTATTTCTGG GCATGTCTTC GAGGGTGTTT CCAGAGGGGA   2042

TTGGCATGCG ATCGGGTGGA CTGAGTGGAA AAGACCTACC CTTAATTTGG GGGGGCACCG   2102

TCCGACAGAC TGGGGAGCAA GATAGAAGAA AACAAAAAAA AAAAAAAAA              2152

(2) INFORMATION FOR SEQ ID NO: 2:

(i) SEQUENCE CHARACTERISTICS:
        (A) LENGTH: 468 amino acids
        (B) TYPE: amino acid
        (D) TOPOLOGY: linear (ii) MOLECULE TYPE: protein (xi) SEQUENCE DESCRIPTION: SEQ ID NO: 2:

Met Ala Pro Pro Ala Arg Val His Leu Gly Ala Phe Leu Ala Val
1               5                   10                  15

Thr Pro Asn Pro Gly Ser Ala Ala Ser Gly Thr Glu Ala Ala Ala
            20                  25                  30

Thr Pro Ser Lys Val Trp Gly Ser Ala Gly Arg Ile Glu Pro Arg
            35                  40                  45

Gly Gly Gly Arg Gly Ala Leu Pro Thr Ser Met Gly Gln His Gly Pro
    50                  55                  60

Ser Ala Arg Ala Arg Ala Gly Arg Ala Pro Gly Pro Arg Pro Ala Arg
65                  70                  75                  80

Glu Ala Ser Pro Arg Leu Arg Val His Lys Thr Phe Lys Phe Val Val
                85                  90                  95

Val Gly Val Leu Leu Gln Val Val Pro Ser Ser Ala Ala Thr Ile Lys
                100                 105                 110

Leu His Asp Gln Ser Ile Gly Thr Gln Gln Trp Glu His Ser Pro Leu
            115                 120                 125

Gly Glu Leu Cys Pro Pro Gly Ser His Arg Ser Glu Arg Pro Gly Ala
        130                 135                 140

Cys Asn Arg Cys Thr Glu Gly Val Gly Tyr Thr Asn Ala Ser Asn Asn
```

```
                  145                 150                 155                 160
Leu Phe Ala Cys Leu Pro Cys Thr Ala Cys Lys Ser Asp Glu Glu Glu
                165                 170                 175
Arg Ser Pro Cys Thr Thr Thr Arg Asn Thr Ala Cys Gln Cys Lys Pro
            180                 185                 190
Gly Thr Phe Arg Asn Asp Asn Ser Ala Glu Met Cys Arg Lys Cys Ser
        195                 200                 205
Thr Gly Cys Pro Arg Gly Met Val Lys Val Lys Asp Cys Thr Pro Trp
    210                 215                 220
Ser Asp Ile Glu Cys Val His Lys Glu Ser Gly Asn Gly His Asn Ile
225                 230                 235                 240
Trp Val Ile Leu Val Val Thr Leu Val Val Pro Leu Leu Leu Val Ala
                245                 250                 255
Val Leu Ile Val Cys Cys Cys Ile Gly Ser Gly Cys Gly Gly Asp Pro
                260                 265                 270
Lys Cys Met Asp Arg Val Cys Phe Trp Arg Leu Gly Leu Leu Arg Gly
            275                 280                 285
Pro Gly Ala Glu Asp Asn Ala His Asn Glu Ile Leu Ser Asn Ala Asp
        290                 295                 300
Ser Leu Ser Thr Phe Val Ser Glu Gln Gln Met Glu Ser Gln Glu Pro
305                 310                 315                 320
Ala Asp Leu Thr Gly Val Thr Val Gln Ser Pro Gly Glu Ala Gln Cys
                325                 330                 335
Leu Leu Gly Pro Ala Glu Ala Glu Gly Ser Gln Arg Arg Arg Leu Leu
                340                 345                 350
Val Pro Ala Asn Gly Ala Asp Pro Thr Glu Thr Leu Met Leu Phe Phe
                355                 360                 365
Asp Lys Phe Ala Asn Ile Val Pro Phe Asp Ser Trp Asp Gln Leu Met
            370                 375                 380
Arg Gln Leu Asp Leu Thr Lys Asn Glu Ile Asp Val Val Arg Ala Gly
385                 390                 395                 400
Thr Ala Gly Pro Gly Asp Ala Leu Tyr Ala Met Leu Met Lys Trp Val
                405                 410                 415
Asn Lys Thr Gly Arg Asn Ala Ser Ile His Thr Leu Leu Asp Ala Leu
            420                 425                 430
Glu Arg Met Glu Glu Arg His Ala Lys Glu Lys Ile Gln Asp Leu Leu
            435                 440                 445
Val Asp Ser Gly Lys Phe Ile Tyr Leu Glu Asp Gly Thr Gly Ser Ala
        450                 455                 460
Val Ser Leu Glu
465

(2) INFORMATION FOR SEQ ID NO: 3:

(i) SEQUENCE CHARACTERISTICS:
        (A) LENGTH: 669 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 3:

Met Leu Gly Ile Trp Thr Leu Leu Pro Leu Val Leu Thr Ser Val Ala
1               5                   10                  15

Arg Leu Ser Ser Lys Ser Val Asn Ala Gln Val Thr Asp Ile Asn Ser
```

-continued

```
                20                  25                  30
Lys Gly Leu Glu Leu Arg Lys Thr Val Thr Val Glu Thr Gln Asn
            35                  40                  45
Leu Glu Gly Leu His His Asp Gly Gln Phe Cys His Lys Pro Cys Pro
         50                  55                  60
Pro Gly Glu Arg Lys Ala Arg Asp Cys Thr Val Asn Gly Asp Glu Pro
 65                  70                  75                  80
Asp Cys Val Pro Cys Gln Glu Gly Lys Glu Tyr Thr Asp Lys Ala His
                 85                  90                  95
Phe Ser Ser Lys Cys Arg Arg Cys Arg Leu Cys Asp Glu Gly His Gly
             100                 105                 110
Leu Glu Val Glu Ile Asn Cys Thr Arg Thr Gln Asn Thr Lys Cys Arg
         115                 120                 125
Cys Lys Pro Asn Phe Phe Cys Asn Ser Thr Val Cys Glu His Cys Asp
     130                 135                 140
Pro Cys Thr Lys Cys Glu His Gly Ile Ile Lys Glu Cys Thr Leu Thr
 145                 150                 155                 160
Ser Asn Thr Lys Cys Lys Glu Glu Gly Ser Arg Ser Asn Leu Gly Trp
                 165                 170                 175
Leu Cys Leu Leu Leu Leu Pro Ile Pro Leu Ile Val Trp Val Lys Arg
             180                 185                 190
Lys Glu Val Gln Lys Thr Cys Arg Lys His Arg Lys Glu Asn Gln Gly
         195                 200                 205
Ser His Glu Ser Pro Thr Leu Asn Pro Glu Thr Val Ala Ile Asn Leu
     210                 215                 220
Ser Asp Val Asp Leu Ser Lys Tyr Ile Thr Thr Ile Ala Gly Val Met
 225                 230                 235                 240
Thr Leu Ser Gln Val Lys Gly Phe Val Arg Lys Asn Gly Val Asn Glu
                 245                 250                 255
Ala Lys Ile Asp Glu Ile Lys Asn Asp Asn Val Gln Asp Thr Ala Glu
             260                 265                 270
Gln Lys Val Gln Leu Leu Arg Asn Trp His Gln Leu His Gly Lys Lys
         275                 280                 285
Glu Ala Tyr Asp Thr Leu Ile Lys Asp Leu Lys Lys Ala Asn Leu Cys
     290                 295                 300
Thr Leu Ala Glu Lys Ile Gln Thr Ile Ile Leu Lys Asp Ile Thr Ser
 305                 310                 315                 320
Asp Ser Glu Asn Ser Asn Phe Arg Asn Glu Ile Gln Ser Leu Val Met
                 325                 330                 335
Leu Gly Ile Trp Thr Leu Leu Pro Leu Val Leu Thr Ser Val Ala Arg
             340                 345                 350
Leu Ser Ser Lys Ser Val Asn Ala Gln Val Thr Asp Ile Asn Ser Lys
         355                 360                 365
Gly Leu Glu Leu Arg Lys Thr Val Thr Val Glu Thr Gln Asn Leu
     370                 375                 380
Glu Gly Leu His His Asp Gly Gln Phe Cys His Lys Pro Cys Pro
 385                 390                 395                 400
Gly Glu Arg Lys Ala Arg Asp Cys Thr Val Asn Gly Asp Glu Pro Asp
                 405                 410                 415
Cys Val Pro Cys Gln Glu Gly Lys Glu Tyr Thr Asp Lys Ala His Phe
             420                 425                 430
Ser Ser Lys Cys Arg Arg Cys Arg Leu Cys Asp Glu Gly His Gly Leu
         435                 440                 445
```

-continued

```
Glu Val Glu Ile Asn Cys Thr Arg Thr Gln Asn Thr Lys Cys Arg Cys
    450                 455                 460

Lys Pro Asn Phe Phe Cys Asn Ser Thr Val Cys Glu His Cys Asp Pro
465                 470                 475                 480

Cys Thr Lys Cys Glu His Gly Ile Ile Lys Glu Cys Thr Leu Thr Ser
                    485                 490                 495

Asn Thr Lys Cys Lys Glu Gly Ser Arg Ser Asn Leu Gly Trp Leu
                500                 505                 510

Cys Leu Leu Leu Pro Ile Pro Leu Ile Val Lys Arg Lys Glu
    515                 520                 525

Val Gln Lys Thr Cys Arg Lys His Arg Lys Glu Asn Gln Gly Ser His
    530                 535                 540

Glu Ser Pro Thr Leu Asn Pro Glu Thr Val Ala Ile Asn Leu Ser Asp
545                 550                 555                 560

Val Asp Leu Ser Lys Tyr Ile Thr Thr Ile Ala Gly Val Met Thr Leu
                    565                 570                 575

Ser Gln Val Lys Gly Phe Val Arg Lys Asn Gly Val Asn Glu Ala Lys
                580                 585                 590

Ile Asp Glu Ile Lys Asn Asp Asn Val Gln Asp Thr Ala Glu Gln Lys
    595                 600                 605

Val Gln Leu Leu Arg Asn Trp His Gln Leu His Gly Lys Lys Glu Ala
    610                 615                 620

Tyr Asp Thr Leu Ile Lys Asp Leu Lys Lys Ala Asn Leu Cys Thr Leu
625                 630                 635                 640

Ala Glu Lys Ile Gln Thr Ile Ile Leu Lys Asp Ile Thr Ser Asp Ser
                    645                 650                 655

Glu Asn Ser Asn Phe Arg Asn Glu Ile Gln Ser Leu Val
                660                 665

(2) INFORMATION FOR SEQ ID NO: 4:

(i) SEQUENCE CHARACTERISTICS:
        (A) LENGTH: 909 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 4:

Met Gly Leu Ser Thr Val Pro Asp Leu Leu Pro Leu Val Leu Leu Glu
1               5                   10                  15

Leu Leu Val Gly Ile Tyr Pro Ser Gly Val Ile Gly Leu Val Pro His
                20                  25                  30

Leu Gly Asp Arg Glu Lys Arg Asp Ser Val Cys Pro Gln Gly Lys Tyr
            35                  40                  45

Ile His Pro Gln Asn Asn Ser Ile Cys Cys Thr Lys Cys His Lys Gly
    50                  55                  60

Thr Tyr Leu Tyr Asn Asp Cys Pro Gly Pro Gly Asp Thr Asp Cys Arg
65                  70                  75                  80

Glu Cys Glu Ser Gly Ser Phe Thr Ala Ser Glu Asn His Leu Arg His
                85                  90                  95

Cys Leu Ser Cys Ser Lys Cys Arg Lys Glu Met Gly Gln Val Glu Ile
                100                 105                 110

Ser Ser Cys Thr Val Asp Arg Asp Thr Val Cys Gly Cys Arg Lys Asn
            115                 120                 125
```

```
Gln Tyr Arg His Tyr Trp Ser Glu Asn Leu Phe Gln Cys Phe Asn Cys
    130                 135                 140
Ser Leu Cys Leu Asn Gly Thr Val His Leu Ser Cys Gln Glu Lys Gln
145                 150                 155                 160
Asn Thr Val Cys Thr Cys His Ala Gly Phe Phe Leu Arg Glu Asn Glu
                165                 170                 175
Cys Val Ser Cys Ser Asn Cys Lys Lys Ser Leu Glu Cys Thr Lys Leu
            180                 185                 190
Cys Leu Pro Gln Ile Glu Asn Val Lys Gly Thr Glu Asp Ser Gly Thr
        195                 200                 205
Thr Val Leu Leu Pro Leu Val Ile Phe Phe Gly Leu Cys Leu Leu Ser
    210                 215                 220
Leu Leu Phe Ile Gly Leu Met Tyr Arg Tyr Gln Arg Trp Lys Ser Lys
225                 230                 235                 240
Leu Tyr Ser Ile Val Cys Gly Lys Ser Thr Pro Glu Lys Glu Gly Glu
                245                 250                 255
Leu Glu Gly Thr Thr Thr Lys Pro Leu Ala Pro Asn Pro Ser Phe Ser
            260                 265                 270
Pro Thr Pro Gly Phe Thr Pro Thr Leu Gly Phe Ser Pro Val Pro Ser
        275                 280                 285
Ser Thr Phe Thr Ser Ser Ser Thr Tyr Thr Pro Gly Asp Cys Pro Asn
    290                 295                 300
Phe Ala Ala Pro Arg Arg Glu Val Ala Pro Pro Tyr Gln Gly Ala Asp
305                 310                 315                 320
Pro Ile Leu Ala Thr Ala Leu Ala Ser Asp Pro Ile Pro Asn Pro Leu
                325                 330                 335
Gln Lys Trp Glu Asp Ser Ala His Lys Pro Gln Ser Leu Asp Thr Asp
            340                 345                 350
Asp Pro Ala Thr Leu Tyr Ala Val Val Glu Asn Val Pro Pro Leu Arg
        355                 360                 365
Trp Lys Glu Phe Val Arg Arg Leu Gly Leu Ser Asp His Glu Ile Asp
    370                 375                 380
Arg Leu Glu Leu Gln Asn Gly Arg Cys Leu Arg Glu Ala Gln Tyr Ser
385                 390                 395                 400
Met Leu Ala Thr Trp Arg Arg Arg Thr Pro Arg Arg Glu Ala Thr Leu
                405                 410                 415
Glu Leu Leu Gly Arg Val Leu Arg Asp Met Asp Leu Leu Gly Cys Leu
            420                 425                 430
Glu Asp Ile Glu Glu Ala Leu Cys Gly Pro Ala Ala Leu Pro Pro Ala
        435                 440                 445
Pro Ser Leu Leu Arg Met Gly Leu Ser Thr Val Pro Asp Leu Leu Leu
    450                 455                 460
Pro Leu Val Leu Leu Glu Leu Leu Val Gly Ile Tyr Pro Ser Gly Val
465                 470                 475                 480
Ile Gly Leu Val Pro His Leu Gly Asp Arg Glu Lys Arg Asp Ser Val
                485                 490                 495
Cys Pro Gln Gly Lys Tyr Ile His Pro Gln Asn Asn Ser Ile Cys Cys
            500                 505                 510
Thr Lys Cys His Lys Gly Thr Tyr Leu Tyr Asn Asp Cys Pro Gly Pro
        515                 520                 525
Gly Gln Asp Thr Asp Cys Arg Glu Cys Glu Ser Gly Ser Phe Thr Ala
    530                 535                 540
```

-continued

```
Ser Glu Asn His Leu Arg His Cys Leu Ser Cys Ser Lys Cys Arg Glu
545                 550                 555                 560

Lys Glu Met Gly Gln Val Glu Ile Ser Ser Cys Thr Val Asp Arg Asp
            565                 570                 575

Thr Val Cys Gly Cys Arg Lys Asn Gln Tyr Arg His Tyr Trp Ser Glu
        580                 585                 590

Asn Leu Phe Gln Cys Phe Asn Cys Ser Leu Cys Leu Asn Gly Thr Val
    595                 600                 605

His Leu Ser Cys Gln Glu Lys Gln Asn Thr Val Cys Thr Cys His Ala
610                 615                 620

Gly Phe Phe Leu Arg Glu Asn Glu Cys Val Ser Cys Ser Asn Cys Lys
625                 630                 635                 640

Lys Ser Leu Glu Cys Thr Lys Leu Cys Leu Pro Gln Ile Glu Asn Val
            645                 650                 655

Lys Gly Thr Glu Asp Ser Gly Thr Thr Val Leu Leu Pro Leu Val Ile
        660                 665                 670

Phe Phe Gly Leu Cys Leu Leu Ser Leu Leu Phe Ile Gly Leu Met Tyr
    675                 680                 685

Arg Tyr Gln Arg Trp Lys Ser Asp Leu Tyr Ser Ile Val Cys Gly Lys
690                 695                 700

Ser Thr Pro Glu Lys Glu Gly Glu Leu Glu Gly Thr Thr Thr Lys Pro
705                 710                 715                 720

Leu Ala Pro Asn Pro Ser Phe Ser Pro Thr Pro Gly Phe Thr Pro Thr
            725                 730                 735

Leu Gly Phe Ser Pro Val Pro Ser Ser Thr Phe Thr Ser Ser Ser Thr
        740                 745                 750

Tyr Thr Pro Gly Asp Cys Pro Asn Phe Ala Ala Pro Arg Arg Glu Val
    755                 760                 765

Ala Pro Pro Tyr Gln Gly Ala Asp Pro Ile Leu Ala Thr Ala Leu Ala
770                 775                 780

Ser Asp Pro Ile Pro Asn Pro Leu Gln Lys Trp Glu Asp Ser Ala His
785                 790                 795                 800

Lys Pro Gln Ser Leu Asp Thr Asp Asp Pro Ala Thr Leu Tyr Ala Val
            805                 810                 815

Val Glu Asn Val Pro Pro Leu Arg Trp Lys Glu Phe Val Arg Arg Leu
        820                 825                 830

Gly Leu Ser Pro His Glu Ile Asp Arg Leu Glu Leu Gln Asn Gly Arg
    835                 840                 845

Cys Leu Arg Glu Ala Gln Tyr Ser Met Leu Ala Thr Trp Arg Arg Arg
850                 855                 860

Thr Pro Arg Arg Glu Ala Thr Leu Glu Leu Leu Gly Arg Val Leu Arg
865                 870                 875                 880

Asp Met Asp Leu Leu Gly Cys Leu Glu Asp Ile Glu Glu Ala Leu Cys
            885                 890                 895

Gly Pro Ala Ala Leu Pro Pro Ala Pro Ser Leu Leu Arg
        900                 905
```

(2) INFORMATION FOR SEQ ID NO: 5:

(i) SEQUENCE CHARACTERISTICS:
        (A) LENGTH: 833 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 5:

```
Met Glu Gln Arg Pro Arg Gly Cys Ala Ala Val Ala Ala Leu Leu
 1               5                  10                  15

Leu Val Leu Leu Gly Ala Arg Ala Gln Gly Gly Thr Arg Ser Pro Arg
            20                  25                  30

Cys Asp Cys Ala Gly Asp Phe His Lys Lys Ile Gly Leu Phe Cys Cys
            35                  40                  45

Arg Gly Cys Pro Ala Gly His Tyr Leu Lys Ala Pro Cys Thr Glu Pro
        50                  55                  60

Cys Gly Asn Ser Thr Cys Leu Val Cys Pro Gln Asp Thr Phe Leu Ala
65                  70                  75                  80

Trp Glu Asn His His Asn Ser Glu Cys Ala Arg Cys Gln Ala Cys Asp
                85                  90                  95

Glu Gln Ala Ser Gln Val Ala Leu Glu Asn Cys Ser Ala Val Ala Asp
            100                 105                 110

Thr Arg Cys Gly Cys Lys Pro Gly Trp Phe Val Glu Cys Gln Val Ser
        115                 120                 125

Gln Cys Val Ser Ser Pro Phe Tyr Cys Gln Pro Cys Leu Asp Cys
    130                 135                 140

Gly Ala Leu His Arg His Thr Arg Leu Leu Cys Ser Arg Arg Asp Thr
145                 150                 155                 160

Asp Cys Gly Thr Cys Leu Pro Gly Phe Tyr Glu His Gly Asp Gly Cys
                165                 170                 175

Val Ser Cys Pro Thr Ser Thr Leu Gly Ser Cys Pro Glu Arg Cys Ala
            180                 185                 190

Ala Val Cys Gly Trp Arg Gln Met Phe Trp Val Gln Val Leu Leu Ala
        195                 200                 205

Gly Leu Val Val Pro Leu Leu Leu Gly Ala Thr Leu Thr Tyr Thr Tyr
210                 215                 220

Arg His Cys Trp Pro His Lys Pro Leu Val Thr Ala Asp Glu Ala Gly
225                 230                 235                 240

Met Glu Ala Leu Thr Pro Pro Ala Thr His Leu Ser Pro Leu Asp
                245                 250                 255

Ser Ala His Thr Leu Leu Ala Pro Pro Asp Ser Ser Glu Lys Ile Cys
            260                 265                 270

Thr Val Gln Leu Val Gly Asn Ser Trp Thr Pro Gly Tyr Pro Glu Thr
        275                 280                 285

Gln Glu Ala Leu Cys Pro Gln Val Thr Trp Ser Trp Asp Gln Leu Pro
    290                 295                 300

Ser Arg Ala Leu Gly Pro Ala Ala Pro Thr Leu Ser Pro Glu Ser
305                 310                 315                 320

Pro Ala Gly Ser Pro Ala Met Met Leu Gln Pro Gly Pro Gln Leu Tyr
                325                 330                 335

Asp Val Met Asp Ala Val Pro Ala Arg Arg Trp Lys Glu Phe Val Arg
            340                 345                 350

Thr Leu Gly Leu Arg Glu Ala Glu Ile Glu Ala Val Glu Val Glu Ile
        355                 360                 365

Gly Arg Phe Arg Asp Gln Gln Tyr Glu Met Leu Lys Arg Trp Arg Gln
    370                 375                 380

Gln Gln Pro Ala Gly Leu Gly Ala Val Tyr Ala Ala Leu Glu Arg Met
385                 390                 395                 400

Gly Leu Asp Gly Cys Val Glu Asp Leu Arg Ser Arg Leu Gln Arg Gly
```

```
                    405                 410                 415
Pro Met Glu Gln Arg Pro Arg Gly Cys Ala Ala Val Ala Ala Ala Leu
                420                 425                 430
Leu Leu Val Leu Leu Gly Ala Arg Ala Gln Gly Gly Thr Arg Ser Pro
            435                 440                 445
Arg Cys Asp Cys Ala Gly Asp Phe His Lys Lys Ile Gly Leu Phe Cys
        450                 455                 460
Cys Arg Gly Cys Pro Ala Gly His Tyr Leu Lys Ala Pro Cys Thr Glu
465                 470                 475                 480
Pro Cys Gly Asn Ser Thr Cys Leu Val Cys Pro Gln Asp Thr Phe Leu
                485                 490                 495
Ala Trp Glu Asn His His Asn Ser Glu Cys Ala Arg Cys Gln Ala Cys
            500                 505                 510
Asp Glu Ala Ser Gln Val Ala Leu Glu Asn Cys Ser Ala Val Ala Asp
        515                 520                 525
Thr Arg Cys Gly Cys Lys Pro Gly Trp Phe Val Glu Cys Gln Val Ser
    530                 535                 540
Gln Cys Val Ser Ser Ser Pro Phe Tyr Cys Gln Pro Cys Leu Asp Cys
545                 550                 555                 560
Gly Ala Leu His Arg His Thr Arg Leu Leu Cys Ser Arg Arg Asp Thr
                565                 570                 575
Asp Cys Gly Thr Cys Leu Pro Gly Phe Tyr Glu His Gly Asp Gly Cys
            580                 585                 590
Val Ser Cys Pro Thr Ser Thr Leu Gly Ser Cys Pro Glu Arg Cys Ala
        595                 600                 605
Ala Val Cys Gly Trp Arg Gln Met Phe Trp Val Gln Val Leu Leu Ala
    610                 615                 620
Gly Leu Val Val Pro Leu Leu Leu Gly Ala Thr Leu Thr Tyr Thr Tyr
625                 630                 635                 640
Arg His Cys Trp Pro His Lys Pro Leu Val Thr Ala Asp Glu Ala Gly
                645                 650                 655
Met Glu Ala Leu Thr Pro Pro Ala Thr His Leu Ser Pro Leu Asp
            660                 665                 670
Ser Ala His Thr Leu Leu Ala Pro Pro Asp Ser Ser Glu Lys Ile Cys
        675                 680                 685
Thr Val Gln Leu Val Gly Asn Ser Trp Thr Pro Gly Tyr Pro Glu Thr
    690                 695                 700
Gln Glu Ala Leu Cys Pro Gln Val Thr Trp Ser Trp Asp Gln Leu Pro
705                 710                 715                 720
Ser Arg Ala Leu Gly Pro Ala Ala Ala Pro Thr Leu Ser Pro Glu Ser
                725                 730                 735
Pro Ala Gly Ser Pro Ala Met Met Leu Gln Pro Gly Pro Gln Leu Tyr
            740                 745                 750
Asp Val Met Asp Ala Val Pro Ala Arg Arg Trp Lys Glu Phe Val Arg
        755                 760                 765
Thr Leu Gly Leu Arg Glu Ala Glu Ile Glu Ala Val Glu Val Glu Ile
    770                 775                 780
Gly Arg Phe Arg Asp Gln Gln Tyr Glu Met Leu Lys Arg Trp Arg Gln
785                 790                 795                 800
Gln Gln Pro Ala Gly Leu Gly Ala Val Tyr Ala Ala Leu Glu Arg Met
                805                 810                 815
Gly Leu Asp Gly Cys Val Glu Asp Leu Arg Ser Arg Leu Gln Arg Gly
            820                 825                 830
```

Pro (2) INFORMATION FOR SEQ ID NO: 6:

(i) SEQUENCE CHARACTERISTICS:
        (A) LENGTH: 426 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 6:

```
GGCANAGGTN CGTACCTAGC TCACCTGCAA CCATCAAACT TNATGATCAA TCAATTGGCA      60

CACAGCAATG GGAAACATAG CCCTTTGGAA GANTTGTNTC CACCAGGATC TCATAGATCA     120

AAACATCCTG GGAGCCTGTT AACCGGTGCC CCAAAGGNTG GTCAAGGTCA AGGAATTGTT     180

NCGCCCTGGA AGTGAACATC GAGTGTNTCC ACAAAGGATT CAGGCAATGG GACATAAATA     240

TATGGGTGAA TTTTGGTTGT GAACTTTGGT TGNTCCCGTT GNTGTTGNTG GCTGTGCTGA     300

TTGTTTGTTG TTGCATCGGC TTCAGGTTNT GGAGGGGGAC CCAAGTGCAT GGACAGGGTG     360

TGTTTCTGGG GTTTGGGTCT CTTAGAGGGC NTGGGTTANG GCANGTTCAC AAGGGTTTTA     420

GCAANG                                                                426
```

(2) INFORMATION FOR SEQ ID NO: 7:

(i) SEQUENCE CHARACTERISTICS:
        (A) LENGTH: 339 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 7:

```
TGGGGCTGAG GACAATGCTG ACNACGAGAT TCTGAGCAAC GCAGNACTNG CTGTCCACTT      60

TCGTCTNTGN GCAGCAAATG GAAAGCCAGG AGCCGGCAGA TTTGACAGGT GTCACTGTAC     120

AGTCCCCAGG GGAGGCACAG TGTCTGCTGG TGAGTTGGGG ACAGGCCCTT GCAAGACCTT     180

GTGAGGCAGG GGGTGAAGGC CATGNCTCGG CTTCNNNTGG TCAAAGGGGA AGTGGAGCCT     240

GAGGGAGATG GGACTTNAGG GGGACGGNGC TGCGTGGGGA AAAAGCAGCC ACCNTTTGAC     300

AAGGGGGACA GGCATTTTTN CAAATGTGTG CTTNTTGGT                            339
```

(2) INFORMATION FOR SEQ ID NO: 8:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 8:

```
GCGGCATGCA TGATCAATCA ATTGGCAC                                         28
```

(2) INFORMATION FOR SEQ ID NO: 9:

(i) SEQUENCE CHARACTERISTICS:
        (A) LENGTH: 36 base pairs
        (B) TYPE: nucleic acid
        (C) STRANDEDNESS: single -continued (D) TOPOLOGY: linear (ii) MOLECULE TYPE: DNA (genomic)

(xi) SEQUENCE DESCRIPTION: SEQ ID NO: 9:

GCGGGATCCG CCATCATGGC GCCACCACCA GCTAGA                                36

(2) INFORMATION FOR SEQ ID NO: 10:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 10:

GCGGGATCCT CACTCCAAGG ACACGGCAGA GCC                                   33

(2) INFORMATION FOR SEQ ID NO: 11:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 11:

GCGGGATCCT CAATTATGTC CATTGCCTG                                        29

(2) INFORMATION FOR SEQ ID NO: 12:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 12:

GCGAAGCTTT CAATTATGTC CATTGCCTG                                        29

DEATH DOMAIN CONTAINING RECEPTOR-4 ANTIBODIES

The present application is a continuation of U.S. patent appl. Ser. No. 09/448,868, filed Nov. 24, 1999, now U.S. Pat. No. 6,461,823, which is a divisional of U.S. patent appl. Ser. No. 09/013,895, filed Jan. 27, 1998, now U.S. Pat. No. 6,342,363, which claims the benefit of U.S. Provisional Application No. 60/037,829, filed Feb. 5, 1997 and U.S. Provisional Application No. 60/035,722 filed January 28, 1997; each of which are incorporated herein by reference in its entirety.

FIELD OF THE INVENTION

The present invention relates to a novel member of the tumor necrosis factor family of receptors. More specifically, isolated nucleic acid molecules are provided encoding human Death Domain Containing Receptor 4, sometimes herein "DR4". DR4 polypeptides are also provided, as are vectors, host cells and recombinant methods for producing the same. The invention further relates to screening methods for identifying agonists and antagonists of DR4 activity.

BACKGROUND OF THE INVENTION

Many biological actions, for instance, response to certain stimuli and natural biological processes, are controlled by factors, such as cytokines. Many cytokines act through receptors by engaging the receptor and producing an intracellular response.

For example, tumor necrosis factors (TNF) alpha and beta are cytokines which act through TNF receptors to regulate numerous biological processes, including protection against infection and induction of shock and inflammatory disease. The TNF molecules belong to the "TNF-ligand" superfamily, and act together with their receptors or counter-ligands, the "TNF-receptor" superfamily. So far, nine members of the TNF ligand superfamily have been identified and ten members of the TNF-receptor superfamily have been characterized.

Among the ligands there are included TNF-$\alpha$, lymphotoxin-$\alpha$ (LT-$\alpha$, also known as TNF-$\beta$), LT-$\beta$ (found in complex heterotrimer LT-$\alpha$2-$\beta$), FasL, CD40L, CD27L, CD30L, 4-IBBL, OX40L and nerve growth factor (NGF). The superfamily of TNF receptors includes the p55TNF receptor, p75TNF receptor, TNF receptor-related protein, FAS antigen or APO-1, CD40, CD27, CD30, 4-IBB, OX40, low affinity p75 and NGF-receptor (Meager, A., *Biologicals*, 22:291–295 (1994)).

Many members of the TNF-ligand superfamily are expressed by activated T-cells, implying that they are necessary for T-cell interactions with other cell types which underlie cell ontogeny and functions. (Meager, A., supra).

Considerable insight into the essential functions of several members of the TNF receptor family has been gained from the identification and creation of mutants that abolish the expression of these proteins. For example, naturally occurring mutations in the FAS antigen and its ligand cause lymphoproliferative disease (Watanabe-Fukunaga, R., et al., *Nature* 356:314 (1992)), perhaps reflecting a failure of programmed cell death. Mutations of the CD40 ligand cause an X-linked immunodeficiency state characterized by high levels of immunoglobulin M and low levels of immunoglobulin G in plasma, indicating faulty T-cell-dependent B-cell activation (Allen, R. C. et al., *Science* 259:990 (1993)). Targeted mutations of the low affinity nerve growth factor receptor cause a disorder characterized by faulty sensory innervation of peripheral structures (Lee, K. F. et al., *Cell* 69:737 (1992)).

TNF and LT-$\alpha$ are capable of binding to two TNF receptors (the 55- and 75-kd TNF receptors). A large number of biological effects elicited by TNF and LT-$\alpha$, acting through their receptors, include hemorrhagic necrosis of transplanted tumors, cytotoxicity, a role in endotoxic shock, inflammation, immunoregulation, proliferation and anti-viral responses, as well as protection against the deleterious effects of ionizing radiation. TNF and LT-$\alpha$ are involved in the pathogenesis of a wide range of diseases, including endotoxic shock, cerebral malaria, tumors, autoimmune disease, AIDS and graft-host rejection (Beutler, B. and Von Huffel, C., *Science* 264:667–668 (1994)). Mutations in the p55 Receptor cause increased susceptibility to microbial infection.

Moreover, an about 80 amino acid domain near the C-terminus of TNFR1 (p55) and Fas was reported as the "death domain," which is responsible for transducing signals for programmed cell death (Tartaglia et al., *Cell* 74:845 (1993)).

Apoptosis, or programmed cell death, is a physiologic process essential to the normal development and homeostasis of multicellular organisms (H. Steller, *Science* 267, 1445–1449 (1995)). Derangements of apoptosis contribute to the pathogenesis of several human diseases including cancer, neurodegenerative disorders, and acquired immune deficiency syndrome (C. B. Thompson, *Science* 267, 1456–1462 (1995)). Recently, much attention has focused on the signal transduction and biological function of two cell surface death receptors, Fas/APO-1 and TNFR-1 (J. L. Cleveland, et al., *Cell* 81, 479–482 (1995); A. Fraser, et al., *Cell* 85, 781–784 (1996); S. Nagata, et al., *Science* 267, 1449–56 (1995)). Both are members of the TNF receptor family which also include TNFR-2, low affinity NGFR, CD40, and CD30, among others (C. A. Smith, et al., *Science* 248, 1019–23 (1990); M. Tewari, et al., in *Modular Texts in Molecular and Cell Biology* M. Purton, Heldin, Carl, Ed. (Chapman and Hall, London, 1995). While family members are defined by the presence of cysteine-rich repeats in their extracellular domains, Fas/APO-1 and TNFR-1 also share a region of intracellular homology, appropriately designated the "death domain", which is distantly related to the *Drosophila* suicide gene, reaper (P. Golstein, et al., *Cell* 81, 185–6 (1995); K. White et al., *Science* 264, 677–83 (1994)). This shared death domain suggests that both receptors interact with a related set of signal transducing molecules that, until recently, remained unidentified. Activation of Fas/APO-1 recruits the death domain-containing adapter molecule FADD/MORTI (A. M. Chinnaiyan, et al., *Cell* 81, 505–12 (1995); M. P. Boldin, et al., *J. Biol Chem* 270, 7795–8 (1995); F. C. Kischkel, et al., *EMBO* 14, 5579–5588 (1995)), which in turn binds and presumably activates FLICE/MACH1, a member of the ICE/CED-3 family of pro-apoptotic proteases (M. Muzio et al., *Cell* 85, 817–827 (1996); M. P. Boldin, et al., *Cell* 85, 803–815 (1996)). While the central role of Fas/APO-1 is to trigger cell death, TNFR-1 can signal an array of diverse biological activities-many of which stem from its ability to activate NF-kB (L. A. Tartaglia, et al., *Immunol Today* 13, 151–3 (1992)). Accordingly, TNFR-1 recruits the multivalent adapter molecule TRADD, which like FADD, also contains a death domain (H. Hsu, et al., *Cell* 81, 495–504 (1995); H. Hsu, et al., *Cell* 84, 299–308 (1996)). Through its associations with a number of signaling molecules including FADD, TRAF2, and RIP, TRADD can signal both apoptosis and NF-kB activation (H. Hsu, et al., *Cell* 84, 299–308 (1996); H. Hsu, et al., *Immunity* 4, 387–396 (1996)).

Recently a new apoptosis inducing ligand was discovered. Wiley, S. R. et al., refer to the new molecule as TNF-related apoptosis-inducing ligand or ("TRAIL")(Immunity 3:673–682 (1995)). Pitti, R. M. et al., refer to the new molecule as Apo-2 ligand or ("Apo-2L"). This molecule was also disclosed in copending U.S. Provisional Patent Application Ser. No. 60/013405. For convenience, it will be referred to herein as TRAIL.

Unlike FAS ligand whose transcripts appear to be largely restricted to stimulated T-cells, significant levels of TRAIL are seen in many tissues, and it is constitutively transcribed by some cell lines. It has been shown that TRAIL acts independently from FAS ligand (Wiley, S. R., et al., (1995)), supra). Studies by Marsters, S. A. et al., have indicated that TRAIL activates apoptosis rapidly, within a time frame that is similar to death signaling by FAS/Apo-1L but much faster than TNF-induced apoptosis (Current Biology, 6:750–752 (1996)). All work to date suggest that the receptor for TRAIL is not one of the many known TNF-receptors.

The effects of TNF family ligands and TNF family receptors are varied and influence numerous functions, both normal and abnormal, in the biological processes of the mammalian system. There is a clear need, therefore, for identification and characterization of such receptors and ligands that influence biological activity, both normally and in disease states. In particular, there is a need to isolate and characterize the receptor for the newly discovered TRAIL ligand.

SUMMARY OF THE INVENTION

The present invention provides for isolated nucleic acid molecules comprising nucleic acid sequences encoding the amino acid sequence shown in FIG. 1 (SEQ ID NO:2) or the amino acid sequence encoding the cDNA clone deposited as ATCC Deposit No. 97853 on Jan. 21, 1997.

The present invention also provides vectors and host cells for recombinant expression of the nucleic acid molecules described herein, as well as to methods of making such vectors and host cells and for using them for production of DR4 polypeptides or peptides by recombinant techniques.

The invention further provides an isolated DR4 polypeptide having an amino acid sequence encoded by a polynucleotide described herein.

The present invention also provides diagnostic assays such as quantitative and diagnostic assays for detecting levels of DR4 protein. Thus, for instance, a diagnostic assay in accordance with the invention for detecting overexpression of DR4, or soluble form thereof, compared to normal control tissue samples may be used to detect the presence of tumors.

Tumor Necrosis Factor (TNF) family ligands are known to be among the most pleiotropic cytokines, inducing a large number of cellular responses, including cytotoxicity, antiviral activity, immunoregulatory activities, and the transcriptional regulation of several genes. Cellular response to TNF-family ligands include not only normal physiological responses, but also diseases associated with increased apoptosis or the inhibition of apoptosis. Apoptosis-programmed cell death-is a physiological mechanism involved in the deletion of peripheral T lymphocytes of the immune system, and its dysregulation can lead to a number of different pathogenic processes. Diseases associated with increased cell survival, or the inhibition of apoptosis, include cancers, autoimmune disorders, viral infections, inflammation, graft v. host disease, acute graft rejection, and chronic graft rejection. Diseases associated with increased apoptosis include AIDS, neurodegenerative disorders, myelodysplastic syndromes, ischemic injury, toxin-induced liver disease, septic shock, cachexia and anorexia.

Thus, the invention further provides a method for enhancing apoptosis induced by a TNF-family ligand, which involves administering to a cell which expresses the DR4 polypeptide an effective amount of an agonist capable of increasing DR4 mediated signaling. Preferably, DR4 mediated signaling is increased to treat a disease wherein decreased apoptosis is exhibited.

In a further aspect, the present invention is directed to a method for inhibiting apoptosis induced by a TNF-family ligand, which involves administering to a cell which expresses the DR4 polypeptide an effective amount of an antagonist capable of decreasing DR4 mediated signaling. Preferably, DR4 mediated signaling is decreased to treat a disease wherein increased apoptosis is exhibited.

Whether any candidate "agonist" or "antagonist" of the present invention can enhance or inhibit apoptosis can be determined using art-known TNF-family ligand/receptor cellular response assays, including those described in more detail below. Thus, in a further aspect, a screening method is provided for determining whether a candidate agonist or antagonist is capable of enhancing or inhibiting a cellular response to a TNF-family ligand. The method involves contacting cells which express the DR4 polypeptide with a candidate compound and a TNF-family ligand, assaying a cellular response, and comparing the cellular response to a standard cellular response, the standard being assayed when contact is made with the ligand in absence of the candidate compound, whereby an increased cellular response over the standard indicates that the candidate compound is an agonist of the ligand/receptor signaling pathway and a decreased cellular response compared to the standard indicates that the candidate compound is an antagonist of the ligand/receptor signaling pathway. By the invention, a cell expressing the DR4 polypeptide can be contacted with either an endogenous or exogenously administered TNF-family ligand.

BRIEF DESCRIPTION OF THE DRAWINGS

FIGS. 1A–1C show the nucleotide sequence (SEQ ID NO:1) and deduced amino acid sequence (SEQ ID NO:2) of DR4. It is predicted that amino acids 1–23 constitute the signal peptide, amino acids 24–238 constitute the extracellular domain, amino acids 239–264 constitute the transmembrane domain, and amino acids 265–468 constitute the intracellular domain of which amino acids 379–422 constitute the death domain.

FIGS. 2A–2C show the regions of similarity between the amino acid sequences of DR4, (SEQ ID NO:2) human tumor necrosis actor receptor 1 (SEQ ID NO:3), human Fas protein (SEQ ID NO:4), and the death domain containing receptor 3 (DR3)(SEQ ID NO:5).

FIG. 4 shows the nucleotide sequences of related nucleic acid fragments HTOIY07R (SEQ ID NO:6) and HTXEY80R (SEQ ID NO:7).

DETAILED DESCRIPTION OF THE PREFERRED EMBODIMENTS

Figure 2A:
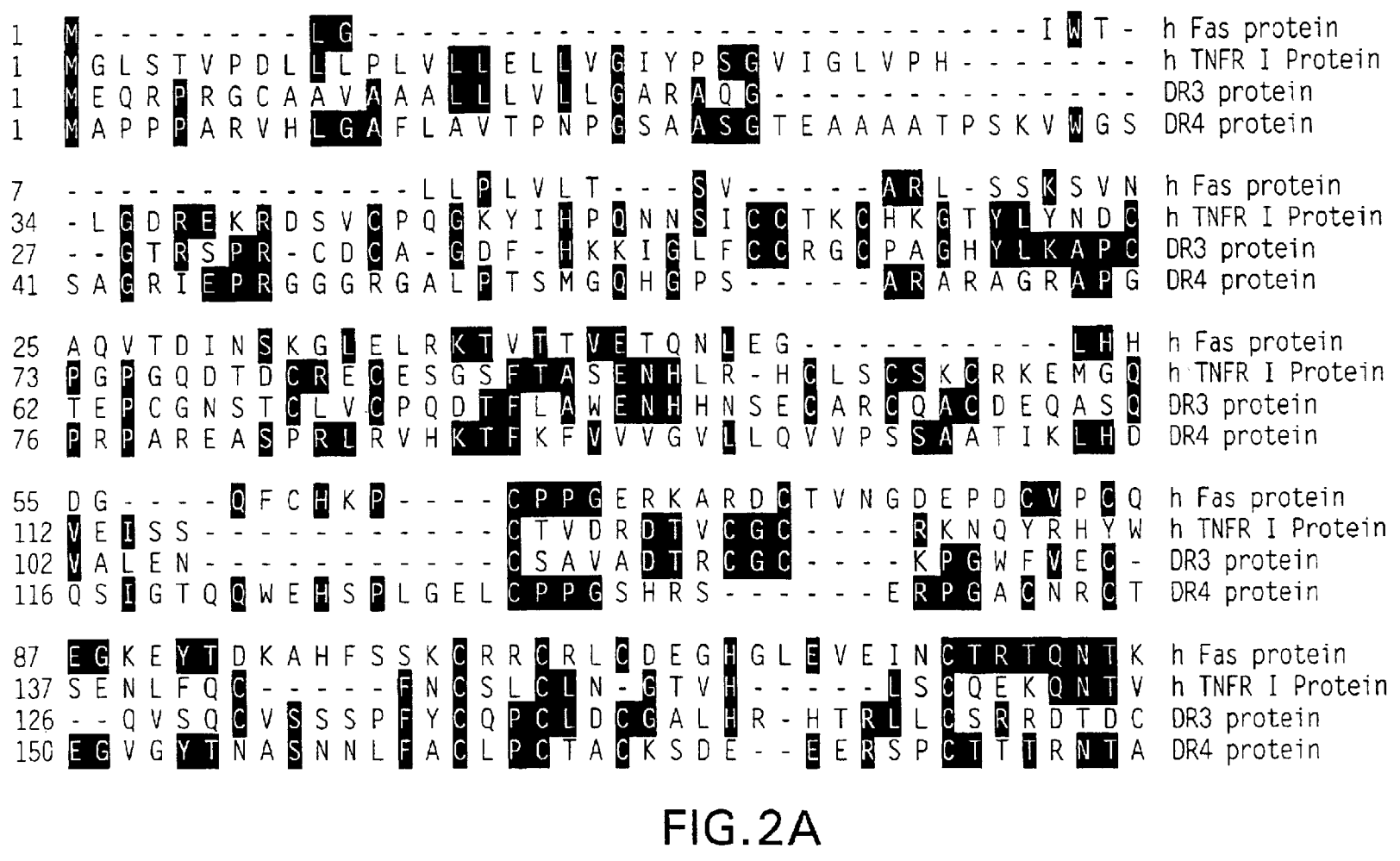
Figure 3:
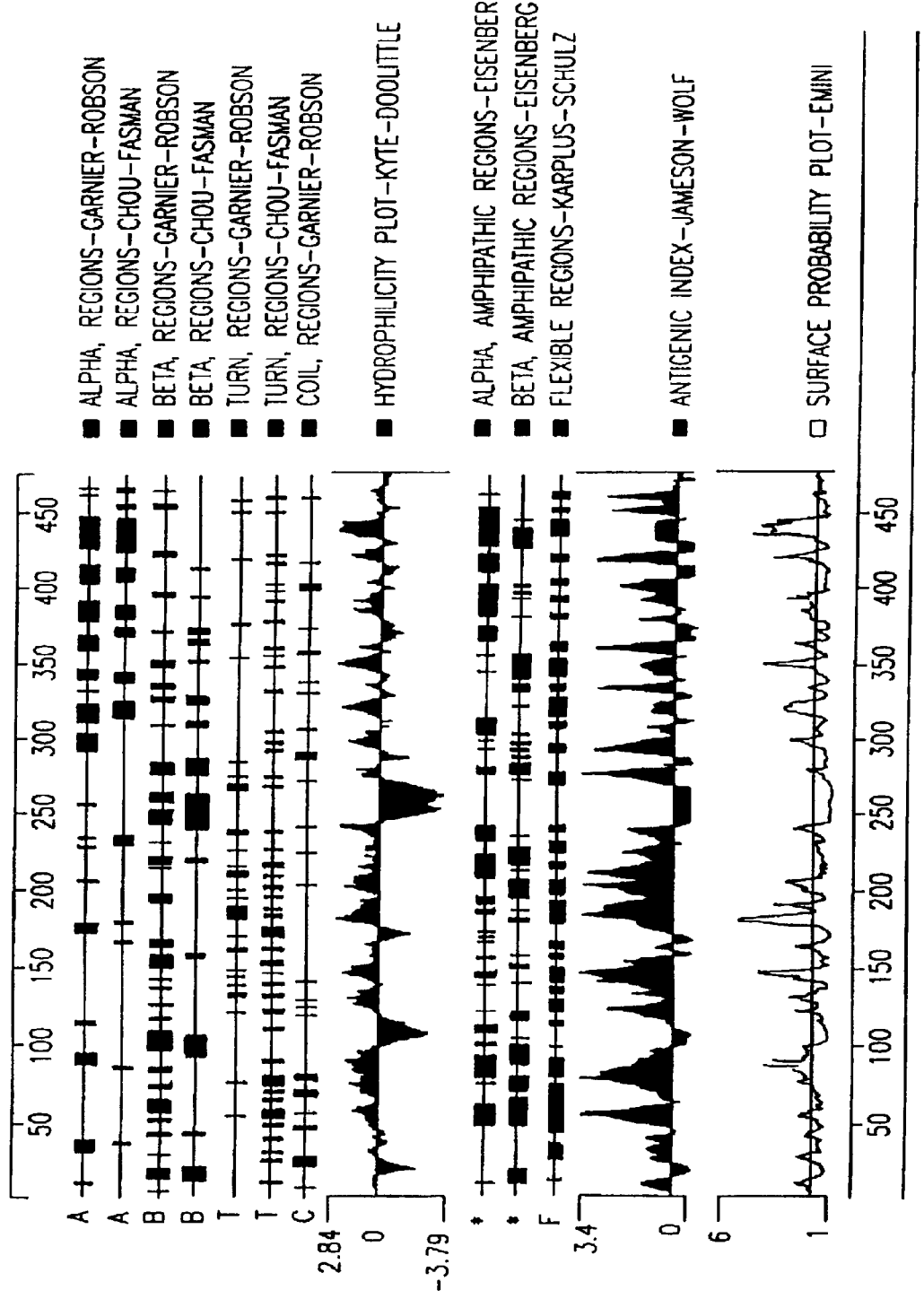
FIG. 3 shows an analysis of the DR4 amino acid sequence. Alpha, beta, turn and coil regions; hydrophilicity and hydrophobicity; amphipathic regions; flexible regions; antigenic index and surface probability are shown. In the "Antigenic Index—Jameson-Wolf" graph, amino acid residues 35–92, 114–160, 169–240, 267–298, 330–364, 391–404, and 418–465 in FIG. 1 correspond to the shown highly antigenic regions of the DR4 protein.

The present invention provides isolated nucleic acid molecules comprising, or alternatively consisting of, a nucleic acid sequence encoding the DR4 polypeptide whose amino acid sequence is shown in SEQ ID NO:2, or a fragment of the polypeptide. The DR4 polypeptide of the present invention shares sequence homology with human TNFR-I, DR3 and Fas ligand (FIG. 2). The nucleotide sequence shown in SEQ ID NO:1 was obtained by sequencing cDNA clones such as HCUDS60, which was deposited on Jan. 21, 1997 at the American Type Culture Collection, 10801 University Boulevard, Manassas, Va., 20110-2209, and given Accession Number 97853. The deposited clone is contained in the pBK plasmid (Stratagene, Lajolla, Calif.).

Nucleic Acid Molecules

Unless otherwise indicated, all nucleotide sequences determined by sequencing a DNA molecule herein were determined using an automated DNA sequencer (such as the Model 373 from Applied Biosystems, Inc.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

By "isolated" polypeptide or protein is intended a polypeptide or protein removed from its native environment. For example, recombinantly produced polypeptides and proteins expressed in host cells are considered isolated for purposed of the invention as are native or recombinant polypeptides which have been substantially purified by any suitable technique such as, for example, the single-step purification method disclosed in Smith and Johnson, Gene 67:3140 (1988).

Using the information provided herein, such as the nucleic acid sequence set out in FIGS. 1A–1C, a nucleic acid molecule of the present invention encoding a DR4 polypeptide may be obtained using standard cloning and screening procedures, such as those for cloning cDNAs using mRNA as starting material. Illustrative of the invention, the gene of the present invention has also been identified in cDNA libraries of the following tissues: amniotic cells, heart, liver cancer, kidney, leukocyte, activated T-cell, K562 plus PMA, W138 cells, Th2 cells, human tonsils, and CD34 depleted buffy coat (cord blood).

The DR4 gene contains an open reading frame encoding a mature protein of about 445 amino acid residues whose initiation codon is at position 19–21 of the nucleotide sequence shown in FIGS. 1A–1C (SEQ ID NO.1), with a leader sequence of about 23 amino acid residues (i.e., a total protein length of 468 amino acids), and a deduced molecular weight of about 50 kDa. Of known members of the TNF receptor family, the DR4 polypeptide of the invention shares the greatest degree of homology with human TNFRI and DR3 polypeptides shown in FIG. 2, including significant sequence homology over the multiple Cysteine Rich domains.

Figure 5A:
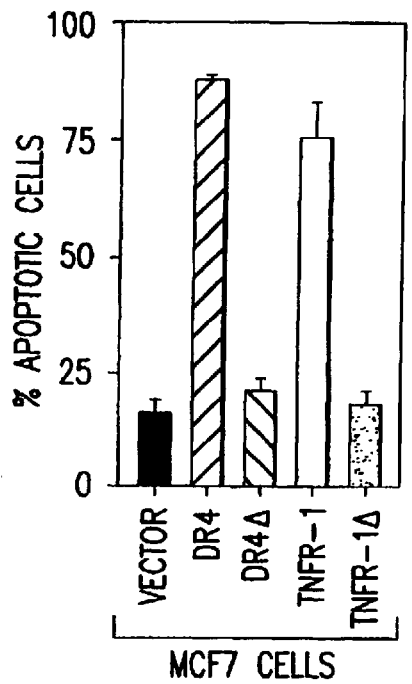
FIGS. 5A and 5B show the ability of DR4 to induce apoptosis in the cell lines MCF7 and 293.
Figure 5B:
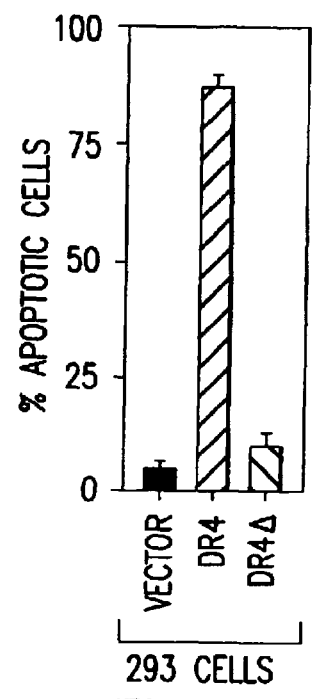
Figure 5C:
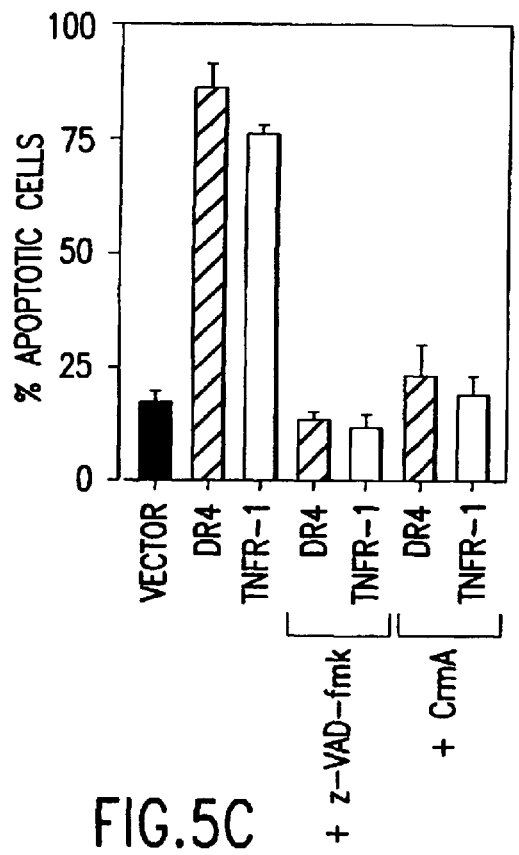
FIG. 5C shows the ability of death protease inhibitors z-VAD-fmk and CrmA to inhibit the apoptotic action of DR4.

In addition to the sequence homology exhibited between DR4 and other death domain containing receptors, DR4 has been shown to bind to TRAIL and to induce apoptosis when transiently expressed. MCF7 human breast carcinoma cells and 293 cells were transiently transfected with a DR4 expressing construct, as described in Example 5. As shown in FIGS. 5A and 5B a substantial proportion of transfected cells underwent the morphological changes characteristic of apoptosis. As anticipated, deletion of the death domain abolished the ability of DR4 to engage the death pathway. As can be seen in FIG. 5C, DR4-induced apoptosis was efficiently blocked by inhibitors of death proteases including z-VAD-fmk, an irreversible broad spectrum caspase inhibitor and CrmA, a cowpox virus encoded serpin that preferentially inhibits apical caspases such as FLICE/MACH-1 (caspase-8). Since TNFR-l, CD-95 and DR3-induced apoptosis is also attenuated by these same inhibitors, it is likely that the downstream death effector molecules are similar in nature.

To determine if DR4 was capable of binding TRAIL, the extracellular ligand binding domain of DR4 was expressed as a fusion to the Fc region of human IgG (DR4-Fc). TRAIL selectively bound to DR4-Fc but not to corresponding, extracellular domains of TNFR-1 or CD-95, also expressed as Fc fusions, data not shown. Additionally, DR4-Fc did not bind either TNF alpha or Fas ligand under conditions where both of these ligands bound their cognate receptors.

Figure 6A:
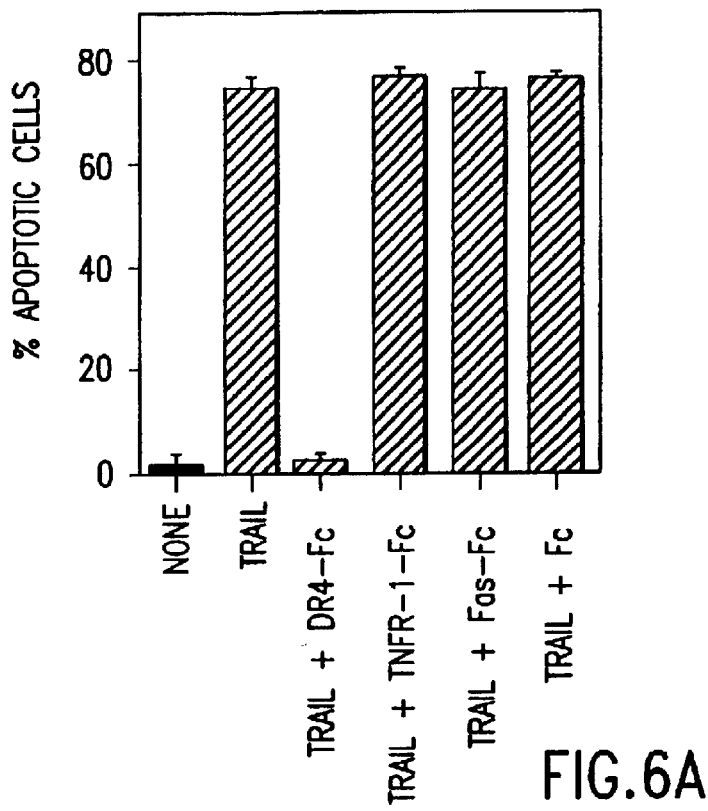
FIG. 6A shows the ability of a soluble extracellular DR4-Fc fusion to block the apoptotic inducing ability of TRAIL.
Figure 6B:
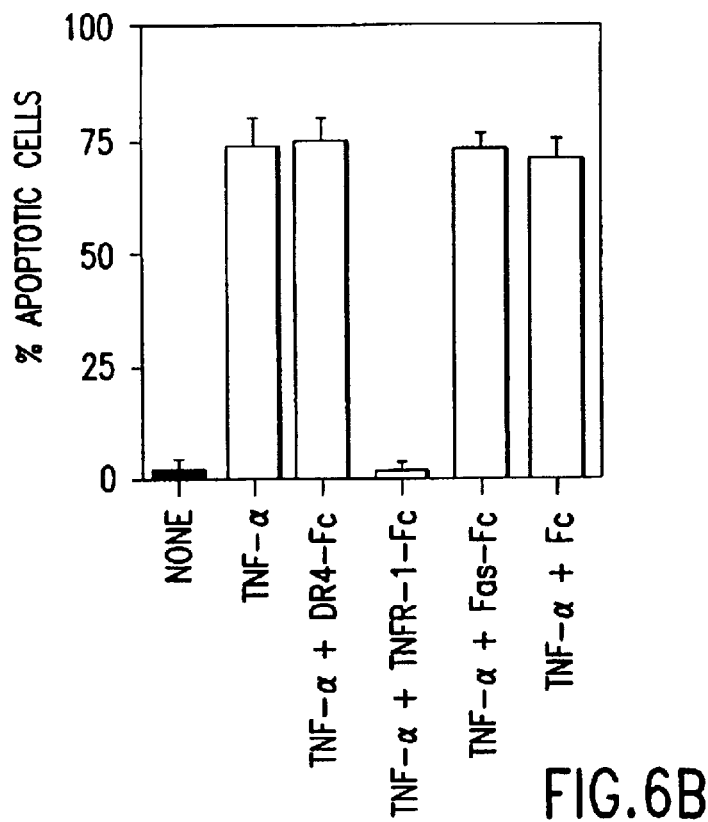
FIG. 6B shows the inability of soluble extracellular DR4-Fc fusion to block the apoptotic inducing ability of TNF-alpha.

The ability of TRAIL to induce apoptosis in MCF7 cells was specifically blocked by DR4-Fc but not influenced by TNFR1-Fc, CD95-Fc or Fc alone (FIG. 6A). Further, as expected, TNF alpha-induced apoptosis was inhibited by TNFR-1-Fc but not by DR4-Fc, CD95-Fc or Fc alone (FIG. 6B).

Taken together, the data described above indicate that DR4 is a death domain containing receptor with the ability to induce apoptosis and is a receptor for TRAIL a known apoptosis inducing ligand.

As indicated, the present invention also provides the mature form(s) of the DR4 protein of the present invention. According to the signal hypothesis, proteins secreted by mammalian cells have a signal or secretory leader sequence which is cleaved from the mature protein once export of the growing protein chain across the rough endoplasmic reticulum has been initiated. Most mammalian cells and even insect cells cleave secreted proteins with the same specificity. However, in some cases, cleavage of a secreted protein is not entirely uniform, which results in two or more mature species on the protein. Further, it has long been known that the cleavage specificity of a secreted protein is ultimately determined by the primary structure of the complete protein, that is, it is inherent in the amino acid sequence of the polypeptide. Therefore, the present invention provides a nucleotide sequence encoding the mature DR4 polypeptide having the amino acid sequence encoded by the cDNA clones contained in the host identified as ATCC Deposit No.

97853, and as shown in FIGS. 1A–1C (SEQ ID NO:2). By the mature DR4 protein having the amino acid sequence encoded by the cDNA clones contained in the host identified as ATCC Deposit No. 97853, is meant the mature form(s) of the DR4 protein produced by expression in a mammalian cell (e.g., COS cells, as described below) of the complete open reading frame encoded by the human DNA sequence of the clone contained in the vector in the deposited host. As indicated below, the mature DR4 having the amino acid sequence encoded by the cDNA clone contained in ATCC Deposit No. 97853, may or may not differ from the predicted "mature" DR4 protein shown in FIGS. 1A–1C (amino acids from about 24 to about 468) depending on the accuracy of the predicted cleavage site based on computer analysis.

Methods for predicting whether a protein has a secretory leader as well as the cleavage point for that leader sequence are available. For instance, the method of McGeoch (*Virus Res.* 3:271–286 (1985)) and von Heinje (*Nucleic Acids Res.* 14:4683–4690 (1986)) can be used. The accuracy of predicting the cleavage points of known mammalian secretory proteins for each of these methods is in the range of 75–80%. von Heinje, supra. However, the two methods do not always produce the same predicted cleavage point(s) for a given protein.

In the present case, the predicted amino acid sequence of the complete DR4 polypeptide of the present invention was analyzed by a computer program ("PSORT"). (See K. Nakai and M. Kanehisa, *Genomics* 14:897–911(1992)), which is an expert system for predicting the cellular location of a protein based on the amino acid sequence. As part of this computational prediction of localization, the methods of McGeoch and von Heinje are incorporated. The analysis by the PSORT program predicted the cleavage sites between amino acids 23 and 24 in FIG. 1A SEQ ID NO:2. Thereafter, the complete amino acid sequences were further analyzed by visual inspection, applying a simple form of the (−1, −3) rule of von Heine. von Heinje, supra. Thus, the leader sequence for the DR4 protein is predicted to consist of amino acid residues 1–23, underlined in FIG. 1A SEQ ID NO:2, while the predicted mature DR4 protein consists of about residues 24–468.

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Isolated nucleic acid molecules of the present invention include DR4 DNA molecules comprising an open reading frame (ORF) shown in FIGS. 1A–1C (SEQ ID NO:1) and further include DNA molecules which comprise a sequence substantially different than all or part of the ORF whose initiation codon is at position 19–21 of the nucleotide sequence shown in FIGS. 1A–1C (SEQ ID NO:1) but which, due to the degeneracy of the genetic code, still encode the DR4 polypeptide or a fragment thereof. Of course, the genetic code is well known in the art. Thus, it would be routine for one skilled in the art to generate such degenerate variants.

In another aspect, the invention provides isolated nucleic acid molecules encoding the DR4 polypeptide having an amino acid sequence encoded by the cDNA clone contained in the plasmid deposited as ATCC Deposit No. 97853 on Jan. 21, 1997. Preferably, these nucleic acid molecules will encode the mature polypeptide encoded by the above-described deposited cDNA clone. The invention further provides an isolated nucleic acid molecule having the nucleotide sequence shown in FIGS. 1A–1C (SEQ ID NO:1) or the nucleotide sequence of the DR4 cDNA contained in the above-described deposited clone, or a nucleic acid molecule having a sequence complementary to one of the above sequences. Such isolated DNA molecules and fragments thereof are useful as DNA probes for gene mapping by in situ hybridization of the DR4 gene in human tissue by Northern blot analysis.

The present invention is further directed to fragments of the isolated nucleic acid molecules described herein. By fragments of an isolated DNA molecule having the nucleotide sequence shown in FIGS. 1A–1C (SEQ ID NO:1) are intended DNA fragments at least 20 bp, and more preferably at least 30 bp in length which are useful as DNA probes as discussed above, of course larger DNA fragments 50–1500 bp in length are also useful as DNA probes according to the present invention as are DNA fragments corresponding to most, if not all, of the nucleotide sequence shown in FIGS. 1A–1C (SEQ ID NO:1). By a fragment at least 20 bp in length, for example, is intended fragments which include 20 or more bases from the nucleotide sequence in FIGS. 1A–1C (SEQ ID NO:1).

Preferred nucleic acid fragments of the present invention include nucleic acid molecules encoding: a polypeptide comprising the DR4 extracellular domain (amino acid residues from about 24 to about 238 in FIG. 1A (SEQ ID NO:2)); a polypeptide comprising the DR4 transmembrane domain (amino acid residues from about 239 to about 264 in FIG. 1B (SEQ ID NO:2)); a polypeptide comprising the DR4 intracellular domain (amino acid residues from about 265 to about 468 in FIGS. 1B and 1C (SEQ ID NO:2)); and a polypeptide comprising the DR4 death domain (amino acid residues from about 379 to about 422 in FIG. 1B (SEQ ID NO:2)). Since the location of these domains have been predicted by computer graphics, one of ordinary skill would appreciate that the amino acid residues constituting these domains may vary slightly (e.g., by about 1 to 15 residues) depending on the criteria used to define the domain.

Preferred nucleic acid fragments of the invention encode a full-length DR4 polypeptide lacking the nucleotides encoding the amino-terminal methionine (nucleotides 19–21 in SEQ ID NO:1) as it is known that the methionine is cleaved naturally and such sequences maybe useful in genetically engineering DR4 expression vectors. Polypeptides encoded by such polynucleotides are also contemplated by the invention.

Preferred nucleic acid fragments of the present invention further include nucleic acid molecules encoding epitope-bearing portions of the DR4 protein. In particular, such nucleic acid fragments of the present invention include nucleic acid molecules encoding: a polypeptide comprising amino acid residues from about 35 to about 92 in FIG. 1A (SEQ ID NO:2); a polypeptide comprising amino acid residues from about 114 to about 160 in FIG. 1A (SEQ ID NO:2); a polypeptide comprising amino acid residues from about 169 to about 240 in FIG. 1A (SEQ ID NO:2); a polypeptide comprising amino acid residues from about 267 to about 298 in FIG. 1B (SEQ ID NO:2); a polypeptide comprising amino acid residues from about 330 to about 364 in FIG. 1B (SEQ ID NO:2); a polypeptide comprising amino acid residues from about 391 to about 404 in FIG. 1B (SEQ ID NO:2); and a polypeptide comprising amino acid residues from about 418 to about 465 in FIGS. 1B and 1C (SEQ ID NO:2). The inventors have determined that the above polypeptide fragments are antigenic regions of the DR4 protein. Methods for determining other such epitope-bearing portions of the DR4 protein are described in detail below.

In addition, the invention provides nucleic acid molecules having nucleotide sequences related to extensive portions of SEQ ID NO:1 as follows: HTOIY07R (SEQ ID NO:6) and HTXEY80R (SEQ ID NO:7) both shown in FIG. 4.

Further, the invention includes a polynucleotide comprising any portion of at least about 30 nucleotides, preferably at least about 50 nucleotides, of SEQ ID NO:1 from residue 365 to 1,424.

In another aspect, the invention provides an isolated nucleic acid molecule comprising a polynucleotide which hybridizes under stringent hybridization conditions to a portion of the polynucleotide in a nucleic acid molecule of the invention described above, for instance, the cDNA clones contained in ATCC Deposit No. 97853. By "stringent hybridization conditions" is intended overnight incubation at 42 C in a solution comprising: 50% formamide, 5×SSC (750 mM NaCl, 75 mM trisodium citrate), 50 mM sodium phosphate (pH 7.6), 5× Denhardt's solution, 10% dextran sulfate, and 20 µg/ml denatured, sheared salmon sperm DNA, followed by washing the filters in 0.1×SSC at about 65° C.

By a polynucleotide which hybridizes to a "portion" of a polynucleotide is intended a polynucleotide (dither DNA or RNA) hybridizing to at least about 15 nucleotides (nt), and more preferably at least about 20 nt, still more preferably at least about 30 nt, and even more preferably about 30–70 nt of the reference polynucleotide. These are useful as diagnostic probes and primers as discussed above and in more detail below.

Figure 2B:
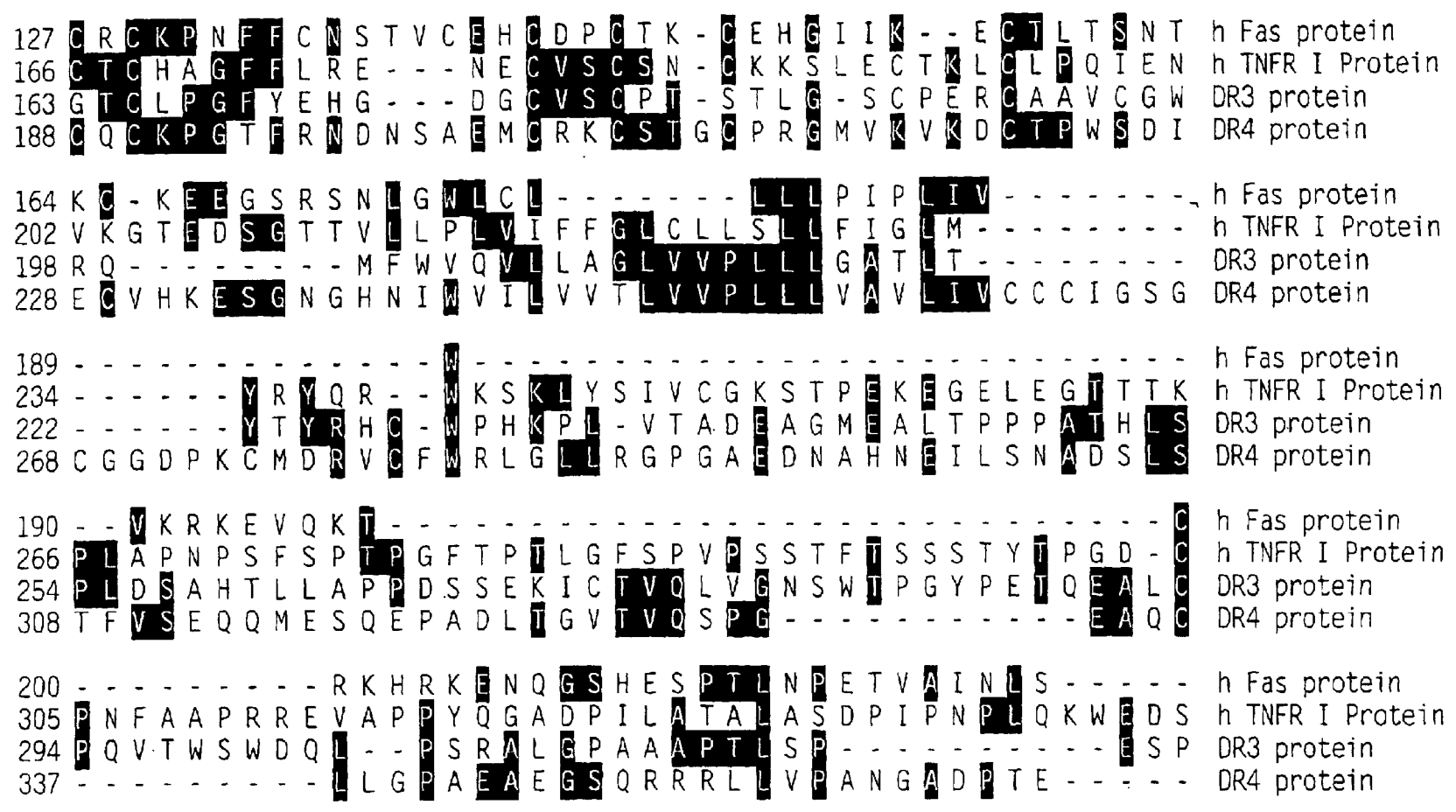
Figure 2C:
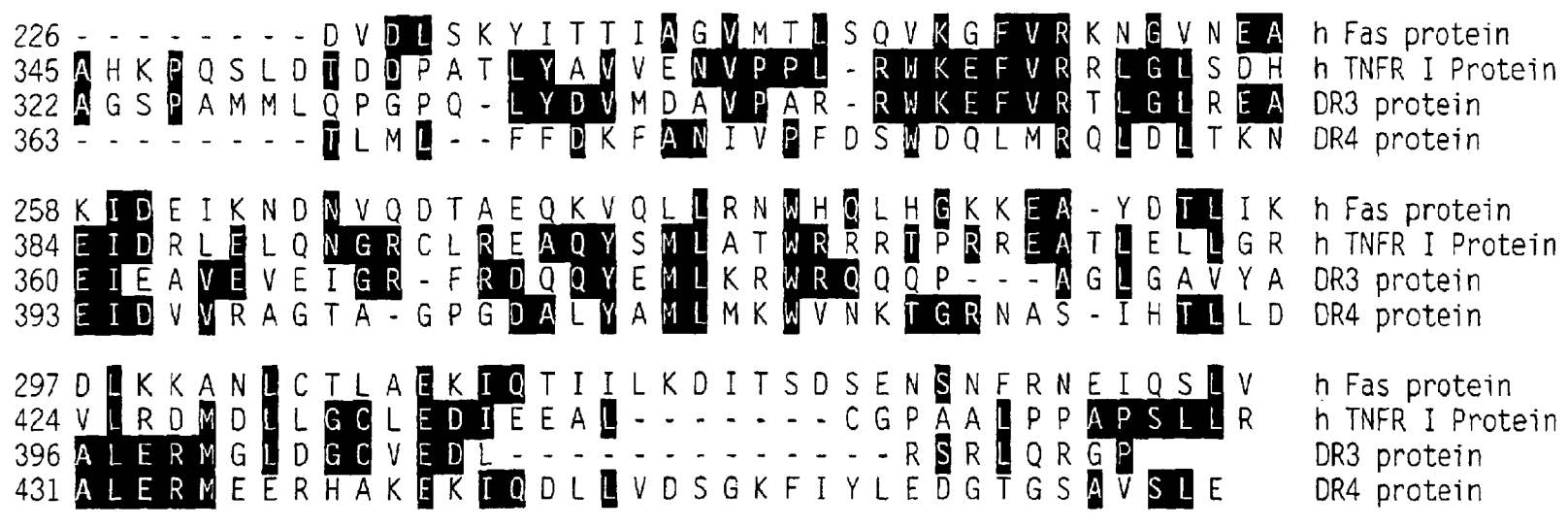

By a portion of a polynucleotide of "at least 20 nt in length," for example, is intended 20 or more contiguous nucleotides from the nucleotide sequence of the reference polynucleotide (e.g., the deposited cDNA or the nucleotide sequence as shown in FIGS. 1A–1C (SEQ ID NO:1) or FIGS. 2A–2C (SEQ ID NO:3).

Of course, a polynucleotide which hybridizes only to a poly A sequence (such as the 3 terminal poly(A) tract of the DR4 cDNA shown in FIG. 1C (SEQ ID NO:1)), or to a complementary stretch of T (or U) resides, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

As indicated, nucleic acid molecules of the present invention which encode the DR4 polypeptide may include, but are not limited to the coding sequence for the mature polypeptide, by itself; the coding sequence for the mature polypeptide and additional sequences, such as those encoding a leader or secretory sequence, such as a pre-, or pro- or prepro- protein sequence; the coding sequence of the mature polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing including splicing and polyadenylation signals, for example—ribosome binding and stability of mRNA; additional coding sequence which codes for additional amino acids, such as those which provide additional functionalities. Thus, for instance, the polypeptide may be fused to a marker sequence, such as a peptide, which facilitates purification of the fused polypeptide. In certain preferred embodiments of this aspect of the invention, the marker sequence is a hexa-histidine peptide, such as the tag provided in a pQE: vector (Qiagen, Inc.), among others, many of which are commercially available. As described in Gentz et al., Proc. Natl. Acad. Sci. USA 86:821–824 (1989), for instance, hexa-histidine provides for convenient purification of the fusion protein. The HA tag corresponds to an epitope derived of influenza hemagglutinin protein, which has been described by Wilson et al., Cell 37:767 (1984), for instance.

The present invention further relates to variants of the nucleic acid molecules of the present invention, which encode for fragments, analogs or derivatives of the DR4 polypeptide. Variants may occur naturally, such as an allelic variant. By an "allelic variant" is intended one of several alternate forms of a gene occupying a given locus on a chromosome of an organism. Genes II, Lewin, B., ed., John Wiley & Sons, New York (1985). Non-naturally occurring variants may be produced using art-known mutagenesis techniques.

Such variants include those produced by nucleotide substitutions, deletions or additions which may involve one or more nucleotides. The variants may be altered in coding or non-coding regions or both. Alterations in the coding regions may produce conservative or non-conservative amino acid substitutions, deletions or additions.

Further embodiments of the invention include isolated nucleic acid molecules that are at least 90% identical, and more preferably at least 95%, 96%, 97%, 98% or 99% identical, to (a) a nucleotide sequence encoding the full-length DR4 polypeptide having the complete amino acid sequence in FIGS. 1A–1C (SEQ ID NO:2), including the predicted leader sequence; (b) nucleotide sequence encoding the full-length DR4 polypeptide having the complete amino acid sequence in FIGS. 1A–1C (SEQ ID NO:2), including the predicted leader sequence but lacking the amino terminal methionine; (c) a nucleotide sequence encoding the mature DR4 polypeptide (full-length polypeptide with the leader removed) having the amino acid sequence at positions about 24 to about 468 in FIGS. 1A–1C (SEQ ID NO:2); (d) a nucleotide sequence encoding the full-length DR4 polypeptide having the complete amino acid sequence including the leader encoded by the cDNA clone contained in ATCC Deposit No. 97853; (e) a nucleotide sequence encoding the full-length DR4 polypeptide having the complete amino acid sequence including the leader but lacking the amino terminal methionine encoded by the cDNA clone contained in ATCC Deposit No. 97853; (f) a nucleotide sequence encoding the mature DR4 polypeptide having the amino acid sequence encoded by the cDNA clone contained in ATCC Deposit No. 97853; (g) a nucleotide sequence that encodes the DR4 extracellular domain, (h) a nucleotide sequence that encodes the DR4 transmembrane domain, (i) a nucleotide sequence that encodes the DR4 intracellular domain, (j) a nucleotide sequence that encodes the DR4 death domain; or (k) a nucleotide sequence complementary to any of the nucleotide sequences in (a), (b), (c), (d), (e), (f), (g), (h), (i), or (j) above.

By a polynucleotide having a nucleotide sequence at least, for example, 95% "identical" to a reference nucleotide sequence encoding a DR4 polypeptide is intended that the nucleotide sequence of the polynucleotide is identical to the reference sequence except that the polynucleotide sequence may include up to five point mutations per each 100 nucleotides of the reference nucleotide sequence encoding the DR4 polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5 or 3 terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 90%, 95%, 96%, 97%, 98% or 99% identical to, for instance, the nucleotide sequence shown in FIGS. 1A–1C or to the nucleotide sequences of the deposited cDNA clone can be determined conventionally using known computer programs such as the Bestfit program (Wisconsin Sequence Analysis Package, Version 8 for Unix, Genetics Computer Group, University Research Park, 575 Science Drive, Madison, Wis. 53711. Bestfit uses the local homology algorithm of Smith and Waterman, *Advances in Applied Mathematics* 2: 482–489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

The present application is directed-to nucleic acid molecules at least 90%, 95%, 96%, 97%, 98% or 99% identical to the nucleic acid sequence shown in FIGS. 1A–1C (SEQ ID NO:1) or to the nucleic acid sequence of the deposited cDNAs, irrespective of whether they encode a polypeptide having DR4 activity. This is because even where a particular nucleic acid molecule does not encode a polypeptide having DR4 activity, one of skill in the art would still know how to use the nucleic acid molecule, for instance, as a hybridization probe or a polymerase chain reaction (PCR) primer. Uses of the nucleic acid molecules of the present invention that do not encode a polypeptide having DR4 activity include, inter alia, (1) isolating the DR4 gene or allelic variants thereof in a cDNA library; (2) in situ hybridization (e.g., "FISH") to metaphase chromosomal spreads to provide precise chromosomal location of the DR4 gene, as described in Verma et al., *Human Chromosomes: A Manual of Basic Techniques*, Pergamon Press, New York (1988); and (3) Northern Blot analysis for detecting DR4 mRNA expression in specific tissues.

Preferred, however, are nucleic acid molecules having sequences at least 90%, 95%, 96%, 97%, 98% or 99% identical to the nucleic acid sequence shown in FIGS. 1A–1C (SEQ ID NO:1) or to the nucleic acid sequence of the deposited cDNAs which do, in fact, encode a polypeptide having DR4 protein activity. By "a polypeptide having DR4 activity" is intended polypeptides exhibiting activity similar, but not necessarily identical, to an activity of the DR4 protein of the invention (either the full-length protein or, preferably, the mature protein), as measured in a particular biological assay. For example, DR4 protein activity can be measured using the cell death assays performed essentially as previously described (A. M. Chinnaiyan, et al., *Cell* 81, 505–12(1995); M. P. Boldin, et al., *J Biol Chem* 270, 7795–8 (1995); F. C. Kischkel, et al., *EMBO* 14, 5579–5588 (1995); A. M. Chinnaiyan, et al., *J Biol Chem* 271, 4961–4965 (1996)) or as set forth in Examples, below. In MCF7 cells, plasmids encoding full-length DR4 or a candidate death domain containing receptors are co-transfected with the pLantern reporter construct encoding green fluorescent protein. Nuclei of cells transfected with DR4 will exhibit apoptotic morphology as assessed by DAPI staining. Similar to TNFR-1 and Fas/APO-1 (M. Muzio, et al., *Cell* 85, 817–827(1996); M. P. Boldin, et al., *Cell* 85, 803–8 15 (1996); M. Tewari, et al., *J Biol Chem* 270, 3255–60 (1995)), DR4-induced apoptosis is blocked by the inhibitors of ICE-like proteases, CrmA and z-VAD-fmk.

Of course, due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequence of the deposited cDNA or the nucleic acid sequence shown in FIGS. 1A–1C (SEQ ID NO:1) will encode a polypeptide "having DR4 protein activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having DR4 protein activity. This is because the skilled artisan is fully aware of amino acid substitutions that are either less likely or not likely to significantly effect protein function (e.g., replacing one aliphatic amino acid with a second aliphatic amino acid).

For example, guidance concerning how to make phenotypically silent amino acid substitutions is provided in Bowie, J. U. et al., "Deciphering the Message in Protein Sequences: Tolerance to Amino Acid Substitutions," *Science* 247:1306–1310 (1990), wherein the authors indicate that proteins are surprisingly tolerant of amino acid substitutions.

Polynucleotide Assays

This invention is also related to the use of the DR4 polynucleotides to detect complementary polynucleotides such as, for example, as a diagnostic reagent. Detection of a mutated form of DR4 associated with a dysfunction will provide a diagnostic tool that can add or define a diagnosis of a disease or susceptibility to a disease which results from under-expression over-expression or altered expression of DR4 or a soluble form thereof, such as, for example, tumors or autoimmune disease.

Individuals carrying mutations in the DR4 gene may be detected at the DNA level by a variety of techniques. Nucleic acids for diagnosis may be obtained from a patient's cells, such as from blood, urine, saliva, tissue biopsy and autopsy material. The genomic DNA may be used directly for detection or may be amplified enzymatically by using PCR prior to analysis. (Saiki et al., *Nature* 324:163–166 (1986)). RNA or cDNA may also be used in the same ways. As an example, PCR primers complementary to the nucleic acid encoding DR4 can be used to identify and analyze DR4 expression and mutations. For example, deletions and insertions can be detected by a change in size of the amplified product in comparison to the normal genotype. Point mutations can be identified by hybridizing amplified DNA to radiolabeled DR4 RNA or alternatively, radiolabeled DR4 antisense DNA sequences. Perfectly matched sequences can be distinguished from mismatched duplexes by RNase A digestion or by differences in melting temperatures.

Sequence differences between a reference gene and genes having mutations also may be revealed by direct DNA sequencing. In addition, cloned DNA segments may be employed as probes to detect specific DNA segments The sensitivity of such methods can be greatly enhanced by appropriate use of PCR or another amplification method. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels, with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., *Science* 230:1242(1985)).

Sequence changes at specific locations also may be revealed by nuclease protection assays, such as RNase and S1 protection or the chemical cleavage method (e.g., Cotton et al., *Proc. Natl. Acad. Sci. USA* 85: 4397–4401 (1985)).

Thus, the detection of a specific DNA sequence may be achieved by methods such as hybridization, RNase protection, chemical cleavage, direct DNA sequencing or the use of restriction enzymes, (e.g., restriction fragment length polymorphisms ("RFLP") and Southern blotting of genomic DNA.

In addition to more conventional gel-electrophoresis and DNA sequencing, mutations also can be detected by in situ analysis.

Chromosome Assays

The sequences of the present invention are also valuable for chromosome identification. The sequence is specifically targeted to and can hybridize with a particular location on an individual human chromosome. The mapping of DNAs to chromosomes according to the present invention is an important first step in correlating those sequences with genes associated with disease.

In certain preferred embodiments in this regard, the cDNA herein disclosed is used to clone genomic DNA of a DR4 gene. This can be accomplished using a variety of well known techniques and libraries, which generally are available commercially. The genomic DNA the is used for in situ chromosome mapping using well known techniques for this purpose.

In addition, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes.

Fluorescence in situ hybridization ("FISH") of a cDNA clone to a metaphase chromosomal spread can be used to provide a precise chromosomal location in one step. This technique can be used with cDNA as short as 50 or 60. For a review of this technique, see Verma et al., *Human Chromosomes: a Manual of Basic Techniques*, Pergamon Press, New York (1988).

Once a sequence has been mapped to a precise chromosomal location, the physical position of the sequence on the chromosome can be correlated with genetic map data. Such data are found, for example, in V. McKusick, *Mendelian Inheritance in Man*, available on line through Johns Hopkins University, Welch Medical Library. The relationship between genes and diseases that have been mapped to the same chromosomal region are then identified through linkage analysis (coinheritance of physically adjacent genes)).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

Vectors and Host Cells

The present invention also relates to vectors which include DNA molecules of the present invention, host cells which are genetically engineered with vectors of the invention and the production of polypeptides of the invention by recombinant techniques.

Host cells can be genetically engineered to incorporate nucleic acid molecules and express polypeptides of the present invention. The polynucleotides may be introduced alone or with other polynucleotides. Such other polynucleotides may be introduced independently, co-introduced or introduced joined to the polynucleotides of the invention.

In accordance with this aspect of the invention the vector may be, for example, a plasmid vector a single or double-stranded phage vector, a single or double-stranded RNA or DNA viral vector. Such vectors may be introduced into cells as polynucleotides, preferably DNA, by well known techniques for introducing DNA and RNA into cell. Viral vectors may be replication competent or replication defective. In the latter case viral propagation generally will occur only in complementing host cells.

Preferred among vectors, in certain respects, are those for expression of polynucleotides and polypeptides of the present invention. Generally, such vectors comprise cis-acting control regions effective for expression in a host operatively linked to the polynucleotide to be expressed. Appropriate trans-acting factors either are supplied by the host, supplied by a complementing vector or supplied by the vector itself upon introduction into the host.

A great variety of expression vectors can be used to express a polypeptide of the invention. Such vectors include chromosomal, episomal and virus-derived vectors e.g., vectors derived from bacterial plasmids, from bacteriophage, from yeast episomes, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids, all may be used for expression in accordance with this aspect of the present invention. Generally, any vector suitable to maintain, propagate or express polynucleotides to express a polypeptide in a host may be used for expression in this regard.

The DNA sequence in the expression vector is operatively linked to appropriate expression control sequence(s)), including, for instance, a promoter to direct mRNA transcription. Representatives of such promoters include the phage lambda PL promoter, the *E. coli* lac. trp and tac promoters, the SV40 early and late promoters and promoters of retroviral LTRs to name just a few of the well-known promoters. In general, expression constructs will contain sites for transcription, initiation and termination, and, in the transcribed region, a ribosome binding site for translation. The coding portion of the mature transcripts expressed by the constructs will include a translation initiating AUG at the beginning and a termination codon (UAA, UGA or UAG) appropriately positioned at the end of the polynucleotides to be translated.

In addition, the constructs may contain control regions that regulate as well as engender expression. Generally, such regions will operate by controlling transcription, such as repressor binding sites and enhancers, among others.

Vectors for propagation and expression generally will include selectable markers. Such markers also may be suitable for amplification or the vectors may contain additional markers for this purpose. In this regard, the expression vectors preferably contain one or more selectable marker genes to provide a phenotypic trait for selection of transformed host cells. Preferred markers include dihydrofolate reductase or neomycin resistance for eukaryotic cell culture, and tetracycline or ampicillin resistance genes for culturing E. coli and other bacteria.

The vector containing the appropriate DNA sequence as described elsewhere herein, as well as an appropriate promoter, and other appropriate control sequences, may be introduced into an appropriate host using a variety of well known techniques suitable to expression therein of a desired polypeptide. Representative examples of appropriate hosts include bacterial cells, such as E. coli, Streptomyces and Salmonella typhimurium cells: fungal cells, such as yeast cells; insect cells such as Drosophila S2 and Spodoptera Sf9 cells; animal cells such as CHO, COS and Bowes melanoma cells; and plant cells. Hosts for of a great variety of expression constructs are well known, and those of skill will be enabled by the present disclosure readily to select a host for expressing a polypeptides in accordance with this aspect of the present invention.

Among vectors preferred for use in bacteria are pQE70, pQE60 and pQE-9, available from Qiagen; pBS vectors, Phagescript vectors, Bluescript vectors, pNH8A, pNH16a, pNH18A, pNH-46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene: and pSVK3. pBPV, pMSG and pSVL available from Pharmacia. These vectors are listed solely by way of illustration of the many commercially available and well known vectors available to those of skill in the art.

Selection of appropriate vectors and promoters for expression in a host cell is a well known procedure and the requisite techniques for expression vector construction, introduction of the vector into the host and expression in the host are routine skills in the art.

The present invention also relates to host cells containing the above-described constructs discussed above. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., Basic Methods in Molecular Biology (1986).

The polypeptide may be expressed in a modified form, such as a fusion protein, and may include not only secretion signals but also additional heterologous functional regions. Thus, for instance, a region of additional amino acids, particularly charged amino acids, may be added to the N-terminus of the polypeptide to improve stability and persistence in the host cell, during purification or during subsequent handling and storage. Also, region also may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize proteins. For example, EP-A-O 464 533 (Canadian counterpart 2045869) discloses fusion proteins comprising various portions of constant region of immunoglobin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as, hIL5- has been fused with Fc portions for the purpose of high-throughput screening assays to identify antagonists of hIL-5. See, D. Bennett et al., Journal of Molecular Recognition, Vol. 8:52–58 (1995) and K. Johanson et al., The Journal of Biological Chemistry, Vol. 270, No. 16:9459–9471 (1995).

The DR4 polypeptides can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Well known techniques for refolding protein may be employed to regenerate active conformation when the polypeptide is denatured during isolation and/or purification.

Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

DR4 polynucleotides and polypeptides may be used in accordance with the present invention for a variety of applications, particularly those that make use of the chemical and biological properties of DR4. Among these are applications in treatment of tumors, resistance to parasites, bacteria and viruses, to induce proliferation of T-cells, endothelial cells and certain hematopoietic cells, to treat restenosis, graft vs. host disease, to regulate anti-viral responses and to prevent certain autoimmune diseases after stimulation of DR4 by an agonist. Additional applications relate to diagnosis and to treatment of disorders of cells, tissues and organisms. These aspects of the invention are discussed further below.

DR4 Polypeptides and Fragments

The invention further provides an isolated DR4 polypeptide having the amino acid sequence shown in FIGS. 1A–1C or a peptide or polypeptide comprising a portion of the above polypeptides.

To improve or alter the characteristics of DR4 polypeptides, protein engineering may be employed. Recombinant DNA technology known to those skilled in the art can be used to create novel mutant proteins or "muteins including single or multiple amino acid substitutions, deletions, additions or fusion proteins. Such modified polypeptides can show, e.g., enhanced activity or increased stability. In addition, they may be purified in higher yields and show better solubility than the corresponding natural polypeptide, at least under certain purification and storage conditions.

For instance, for many proteins, including the extracellular domain of a membrane associated protein or the mature form(s) of a secreted protein, it is known in the art that one or more amino acids may be deleted from the N-terminus or C-terminus without substantial loss of biological function. For instance, Ron et al., *J. Biol. Chem.*, 268:2984–2988 (1993) reported modified KGF proteins that had heparin binding activity even if 3, 8, or 27 amino-terminal amino acid residues were missing. In the present case, since the protein of the invention is a member of the death domain containing receptor (DDCR) polypeptide family, deletions of N-terminal amino acids up to the cysteine residue at position 132 in SEQ ID NO:2 may retain some biological activity such as the ability to induce apoptosis. Polypeptides having further N-terminal deletions including the cysteine residue at position 132 (C-132) in SEQ ID NO:2 would not be expected to retain such biological activities because this residue is conserved among family members, see FIGS. 2A and 2B, and may be required for forming a disulfide bridge to provide structural stability which is needed for receptor binding.

However, even if deletion of one or more amino acids from the N-terminus of a protein results in modification of loss of one or more biological functions of the protein, other biological activities may still be retained. Thus, the ability of the shortened protein to induce and/or bind to antibodies which recognize the complete or extracellular domain of the protein generally will be retained when less than the majority of the residues of the complete or extracellular domain protein are removed from the N-terminus. Whether a particular polypeptide lacking N-terminal residues of a complete protein retains such immunologic activities can readily be determined by routine methods described herein and otherwise known in the art.

Accordingly, the present invention further provides polypeptides having one or more residues deleted from the amino terminus of the amino acid sequence of DR4 shown in SEQ ID NO:2, up to C-132 residue, and polynucleotides encoding such polypeptides. In particular, the present invention provides polypeptides comprising the amino acid sequence of residues n-468 of SEQ ID NO:2, where n is an integer in the range of 24–132 where C-132 is the first residue from the N-terminus of the extracellular domain of the DR4 polypeptide (shown in SEQ ID NO:2) believed to be required for receptor-ligand binding (e.g., TRAIL binding) activity of the DR4 protein. Polynucleotides encoding these polypeptides are, also provided.

Similarly, many examples of biologically functional C-terminal deletion muteins are known. For instance, interferon gamma shows up to ten times higher activities by deleting 8–10 amino acid residues from the carboxy terminus of the protein (Döbeli et al., J. Biotechnology 7:199–216 (1988). In the present case, since the protein of the invention is a member of the DDCR polypeptide family, deletions of C-terminal amino acids up to the cysteine at position 221 (C-221) of SEQ ID NO:2 may retain some biological activity such receptor binding Polypeptides having further C-terminal deletions including C-221 of SEQ ID NO:2 would not be expected to retain such biological activities because this residue is conserved among DDCR family members and is required for forming a disulfide bridge to provide structural stability which is needed for receptor-ligand binding.

However, even if deletion of one or more amino acids from the C-terminus of a protein results in modification of loss of one or more biological functions of the protein, other biological activities may still be retained. Thus, the ability of the shortened protein to induce and/or bind to antibodies which recognize the complete or extracellular domain of the protein generally will be retained when less than the majority of the residues of the complete or extracellular domain are removed from the C-terminus. Whether a particular polypeptide lacking C-terminal residues of a complete protein retains such immunologic activities can readily be determined by routine methods described herein and otherwise known in the art.

Accordingly, the present invention further provides polypeptides having one or more residues from the carboxy terminus of the amino acid sequence of the DR4 shown in SEQ ID NO:2, up to C-221 of SEQ ID NO:2, and polynucleotides encoding such polypeptides. In particular, the present invention provides polypeptides having the amino acid sequence of residues 1-m of the amino acid sequence in SEQ ID NO:2, where m is any integer in the range of 221–468 and residue C-221 is the position of the first residue from the C- terminus of the complete DR4 polypeptide (shown in SEQ ID NO:2) believed to be required for receptor binding activity of the DR4 protein. Polynucleotides encoding these polypeptides also are provided.

The invention also provides polypeptides having one or more amino acids deleted from both the amino and the carboxyl termini, which may be described generally as having residues n-m of SEQ ID NO:2, where n and m are integers as described above.

Also included are a nucleotide sequence encoding a polypeptide consisting of a portion of the complete DR4 amino acid sequence encoded by the cDNA clone contained in ATCC Deposit No. 97853, where this portion excludes from 1 to about 108 amino acids from the amino terminus of the complete amino acid sequence encoded by the cDNA clone contained in ATCC Deposit No. 97853, or from 1 to about 247 amino acids from the carboxy terminus, or any combination of the above amino terminal and carboxy terminal deletions, of the complete amino acid sequence encoded by the EDNA clone contained in ATCC Deposit No. 97853. Polynucleotides encoding all of the above deletion mutant polypeptide forms also are provided.

Preferred amongst the N- and C-terminal deletion mutants are those comprising only a portion of the extracellular domain; i.e., within residues 24–238, since any portion therein is expected to be soluble.

It will be recognized in the art that some amino acid sequence of DR4 can be varied without significant effect of the structure or function of the protein. If such differences in sequence are contemplated, it should be remembered that there will be critical areas on the protein which determine activity Such areas will usually comprise residues which make up the ligand binding site or the death domain, or which form tertiary structures which affect these domains.

Thus, the invention further includes variations of the DR4 protein which show substantial DR4 protein activity or which include regions of DR4 such as the protein fragments discussed below. Such mutants include deletions, insertions, inversions, repeats, and type substitutions. As indicated above, guidance concerning which amino acid changes are likely to be phenotypically silent can be found in Bowie, J. U. et al., Science 247:1306–1310 (1990).

Of particular interest are substitutions of charged amino acids with another charged amino acid and with neutral or negatively charged amino acids. The latter results in proteins with reduced positive charge to improve the characteristics of the DR4 protein. The prevention of aggregation is highly desirable. Aggregation of proteins not only results in a loss of activity but can also be problematic when preparing pharmaceutical formulations, because they can be immunogenic. (Pinckard et al., Clin Exp. Immunol. 2:331–340 (1967); Robbins et al., Diabetes 36:838–845 (1987); Cleland et al. Crit. Rev. Therapeutic Drug Carrier Systems 10:307–377 (1993)).

The replacement of amino acids can also change the selectivity of binding to cell surface receptors. Ostade et al., Nature 361:266–268 (1993) describes certain mutations resulting in selective binding of TNF-alpha to only one of the two known types of TNF receptors. Thus, the DR4 receptor of the present invention may include one or more amino acid substitutions, deletions or additions, either from natural mutations or human manipulation.

As indicated, changes are preferably of a minor nature, such as conservative amino acid substitutions that do not significantly affect the folding or activity of the protein (see Table 1).

TABLE 1

Conservative Amino Acid Substitutions.

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Amino acids in the DR4 protein of the present invention that are essential for function can be identified by methods known in the art, such as site-directed mutagenesis or alanine-scanning mutagenesis (Cunningham and Wells, Science 244:1081–1085 (1989)). The latter procedure introduces single alanine mutations at every residue in the molecule. The resulting mutant molecules are then tested for biological activity such as receptor binding or in vitro, or in vitro proliferative activity. Sites that are critical for ligand-receptor binding can also be determined by structural analysis such as crystallization, nuclear magnetic resonance or photoaffinity labeling (Smith et al., J. Mol. Biol. 224:899–904 (1992) and de Vos et al. Science 255:306–312 (1992)).

The polypeptides of the present invention are preferably provided in an isolated form, and preferably are substantially purified. A recombinantly produced version of the DR4 polypeptide is substantially purified by the one-step method described in Smith and Johnson, Gene 67:3140 (1988).

The polypeptides of the present invention also include the polypeptide encoded by the deposited cDNA including the leader, the mature polypeptide encoded by the deposited the cDNA minus the leader (i.e., the mature protein), the polypeptide of FIGS. 1A–1C (SEQ ID NO:2) including the leader, the polypeptide of FIGS. 1A–1C (SEQ ID NO:2) minus the amino terminal methionine, the polypeptide of FIGS. 1A–1C (SEQ ID NO:2) minus the leader, the extracellular domain, the transmembrane domain, the intracellular domain, the death domain, soluble polypeptides comprising all or part of the extracellular and intracelluar domains but lacking the transmembrane domain as well as polypeptides which are at least 80% identical, more preferably at least 90% or 95% identical, still more preferably at least 96%, 97%, 98% or 99% identical to the polypeptide encoded by the deposited cDNA clones, to the polypeptide of FIGS. 1A–1C (SEQ ID NO:2) and also include portions of such polypeptides with at least 30 amino acids and more preferably at least 50 amino acids.

By a polypeptide having an amino acid sequence at least, for example, 95% "identical" to a reference amino acid sequence of a DR4 polypeptide is intended that the amino acid sequence of the polypeptide is identical to the reference sequence except that the polypeptide sequence may include up to five amino acid alterations per each 100 amino acids of the reference amino acid of the DR4 polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequence shown in FIGS. 1A–1C (SEQ ID NO:2) or to the amino acid sequence encoded by deposited cDNA clones can be determined conventionally using known computer programs such the Bestfit program (Wisconsin Sequence Analysis Package, Version 8 for Unix, Genetics Computer Group, University Research Park, 575 Science Drive, Madison, Wis. 53711. When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

The present inventors have discovered that the DR4 polypeptide is a 468 residue protein exhibiting three main structural domains. First, the ligand binding domain was identified within residues from about 24 to about 238 in FIGS. 1A and 1B. Second, the transmembrane domain was identified within residues from about 239 to about 264 in FIG. 1B. Third, the intracellular domain was identified within residues from about 265 to about 468 in FIGS. 1B and 1C. Importantly, the intracellular domain includes a death domain at residues from about 379 to about 422. Further preferred fragments of the polypeptide shown in FIGS. 1A–1C include the mature protein from residues about 24 to about 468 and soluble polypeptides comprising all or part of the extracellular and intracellular domains but lacking the transmembrane domain.

The invention further provides DR4 polypeptides encoded by the deposited cDNA clone including the leader and DR4 polypeptide fragments selected from the mature protein, the extracellular domain, the transmembrane domain, the intracellular domain, and the death domain.

In another aspect, the invention provides a peptide or polypeptide comprising an epitope-bearing portion of a polypeptide described herein. The epitope of this polypeptide portion is an immunogenic or antigenic epitope of a polypeptide of the invention. An "immunogenic epitope" is defined as a part of a protein that elicits an antibody response when the whole protein is the immunogen. On the other hand, a region of a protein molecule to which an antibody can bind is defined as an "antigenic epitope." The number of immunogenic epitopes of a protein generally is less than the number of antigenic epitopes. See, for instance, Geysen et al., Proc. Natl. Acad. Sci. USA 81:3998–4002 (1983).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G., Shinnick, T. M., Green, N. and Learner, R. A. (1983) Antibodies that react with predetermined sites on proteins. Science 219:660–666. Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals.

Antigenic epitope-bearing peptides and polypeptides of the invention are therefore useful to raise antibodies, including monoclonal antibodies, that bind specifically to a polypeptide of the invention. See, for instance, Wilson et al., Cell 37:767–778 (1984) at 777.

Antigenic epitope-bearing peptides and polypeptides of the invention preferably contain a sequence of at least seven, more preferably at least nine and most preferably between at least about 15 to about 30 amino acids contained within the amino acid sequence of a polypeptide of the invention.

Non-limiting examples of antigenic polypeptides or peptides that can be used to generate DR4-specific antibodies include: a polypeptide comprising amino acid residues from about 35 to about 92 in FIG. 1A (SEQ ID NO:2); a polypeptide comprising amino acid residues from about 114 to about 160 in FIG. 1A (SEQ ID NO:2); a polypeptide comprising amino acid residues from about 169 to about 240 in FIGS. 1A and 1B (SEQ ID NO:2); a polypeptide comprising amino acid residues from about 267 to about 298 in FIG. 1B (SEQ ID NO:2); a polypeptide comprising amino acid residues from about 330 to about 364 in FIG. 1B (SEQ ID NO:2); a polypeptide comprising amino acid residues from about 391 to about 404 in FIGS. 1B and 1C (SEQ ID NO:2); and a polypeptide comprising amino acid residues from about 418 to about 465 in FIG. 1C (SEQ ID NO:2). As indicated above, the inventors have determined that the above polypeptide fragments are antigenic regions of the DR4 protein.

The epitope-bearing peptides and polypeptides of the invention may be produced by any conventional means. Houghten, R. A., "General method for the rapid solid-phase synthesis of large numbers of peptides: specificity of antigen-antibody interaction at the level of individual amino acids," Proc. Natl. Acad. Sci. USA 82:5131–5135 (1985). This "Simultaneous Multiple Peptide Synthesis (SMPS)" process is further described in U.S. Pat. No. 4,631,211 to Houghten et al., (1986).

As one of skill in the art will appreciate, DR4 polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EPA 394,827; Traunecker et al., Nature 331:84–86 (1988)). Fusion proteins that have a disulfide-linked dimeric structure due to the IgG part can also be more efficient in binding and neutralizing other molecules than the monomeric DR4 protein or protein fragment alone (Fountoulakis et al., J Biochem 270:3958–3964 (1995)).

Polypeptide Assays

The present invention also relates to diagnostic assays such as quantitative and diagnostic assays for detecting levels of DR4 protein, or the soluble form thereof, in cells and tissues, including determination of normal and abnormal levels. Thus, for instance, a diagnostic assay in accordance with the invention for detecting over-expression of DR4, or soluble form thereof, compared to normal control tissue samples may be used to detect the presence of tumors, for example. Assay techniques that can be used to determine levels of a protein, such as a DR4 protein of the present invention, or a soluble form thereof, in a sample derived from a host are well-known to those of skill in the art. Such assay methods include radioimmunoassays, competitive-binding assays, Western Blot analysis and ELISA assays.

Assaying DR4 protein levels in a biological sample can occur using any art-known method. Preferred for assaying DR4 protein levels in a biological sample are antibody-based techniques. For example, DR4 protein expression in tissues can be studied with classical immunohistological methods. (Jalkanen, M., et al., J. Cell. Biol. 101:976–985 (1985); Jalkanen, M., et al., J. Cell. Biol. 105:3087–3096 (1987)).

Other antibody-based methods useful for detecting DR4 protein gene expression include immunoassays, such as the enzyme linked immunosorbent assay (ELISA) and the radioimmunoassay (RIA).

Suitable labels are known in the art and include enzyme labels, such as glucose oxidase, radioisotopes, such as iodine ($^{125}$I, $^{121}$I), carbon ($^{14}$C), sulphur ($^{35}$S), tritium ($^{3}$H), indium ($^{112}$In), and technetium ($^{99m}$Tc), and fluorescent labels, such as fluorescein and rhodamine, and biotin.

Therapeutics

The Tumor Necrosis Factor (TNF) family ligands are known to be among the most pleiotropic cytokines, inducing a large number of cellular responses, including cytotoxicity, anti-viral activity, immunoregulatory activities, and the transcriptional regulation of several genes (Goeddel, D. V. et al., Tumor Necrosis Factors: Gene Structure and Biological Activities," *Symp. Quant. Biol.* 51:597–609 (1986), Cold Spring Harbor; Beutler, B., and Cerami, A., *Annu. Rev. Biochem.* 57:505–518 (1988); Old, L. J., *Sci. Am.* 258:59–75 (1988); Fiers, W., *FEBS Lett.* 285:199–224 (1991)). The TNF-family ligands induce such various cellular responses by binding to TNF-family receptors, including the DR4 receptors of the present invention. Cells which express the DR4 polypeptide and are believed to have a potent cellular response to DR4 ligand include amniotic cells, heart, liver cancer kidney, peripheral blood leukocytes, activated T-cells, tissue corresponding to Th2 cells, human tonsils, and CD34 depleted buffy coat (cord blood). By "a cellular response to a TNF-family ligand" is intended any genotypic, phenotypic, and/or morphologic change to a cell, cell line, tissue, tissue culture or patient that is induced by a TNF-family ligand. As indicated, such cellular responses include not only normal physiological responses to TNF-family ligand, but also diseases associated with increased apoptosis or the inhibition of apoptosis. Apoptosis-programmed cell death-is a physiological mechanism involved in the deletion of peripheral T lymphocytes of the immune system, and its dysregulation can lead to a number of different pathogenic processes (Ameisen, J. C., *AXDS* 8:1197–1213 (1994); Krammer, P. H. et al., *Curr. Opin. Immunol.* 6:279–289 (1994)).

Diseases associated with increased cell survival, or the inhibition of apoptosis, include cancers (such as follicular lymphomas, carcinomas with p53 mutations, and hormone-dependent tumors, such as breast cancer, prostrate cancer, Kaposi's sarcoma and ovarian cancer); autoimmune disorders (such as systemic lupus erythematosus and immune-related glomerulonephritis rheumatoid arthritis) and viral infections (such as herpes viruses, pox viruses and adenoviruses), information graft v. host disease, acute graft rejection, and chronic graft rejection. Diseases associated with increased apoptosis include AIDS; neurodegenerative disorders (such as Alzheimer's disease, Parkinson's disease, Amyotrophic lateral sclerosis, Retinitis pigmentosa, Cerebellar degeneration); myelodysplastic syndromes (such as aplastic anemia), ischemic injury (such as that caused by myocardial infarction, stroke and reperfusion injury), toxin-induced liver disease (such as that caused by alcohol), septic shock, cachexia and anorexia.

Thus, in one aspect, the present invention is directed to a method for enhancing apoptosis induced by a TNF-family ligand, which involves administering to a cell which expresses the DR4 polypeptide an effective amount of DR4 ligand, analog or an agonist capable of increasing DR4 mediated signaling. Preferably, DR4 mediated signaling is increased to treat a disease wherein decreased apoptosis or decreased cytokine and adhesion molecule expression is exhibited. An agonist can include soluble forms of DR4 and monoclonal antibodies directed against the DR4 polypeptide.

In a further aspect, the present invention is directed to a method for inhibiting apoptosis induced by a TNF-family ligand, which involves administering to a cell which expresses the DR4 polypeptide an effective amount of an antagonist capable of decreasing DR4 mediated signaling. Preferably, DR4 mediated signaling is decreased to treat a disease wherein increased apoptosis or NfκB expression is exhibited. An antagonist can include soluble forms of DR4 and monoclonal antibodies directed against the DR4 polypeptide.

By "agonist" is intended naturally occurring and synthetic compounds capable of enhancing or potentiating apoptosis. By "antagonist" is intended naturally occurring and synthetic compounds capable of inhibiting apoptosis. Whether any candidate "agonist" or "antagonist" of the present invention can enhance or inhibit apoptosis can be determined using art-known TNF-family ligand/receptor cellular response assays, including those described in more detail below.

One such screening procedure involves the use of melanophores which are transfected to express the receptor of the present invention, Such a screening technique is described in PCT WO 92/01810, published Feb. 6, 1992. Such an assay may be employed, for example, for screening for a compound which inhibits (or enhances) activation of the receptor polypeptide of the present invention by contacting the melanophore cells which encode the receptor with both a TNF-family ligand and the candidate antagonist (or agonist). Inhibition or enhancement of the signal generated by the ligand indicates that the compound is an antagonist or agonist of the ligand/receptor signaling pathway.

Other screening techniques include the use of cells which express the receptor (for example, transfected CHO cells) in a system which measures extracellular pH changes caused by receptor activation, for example, as described in *Science* 246:181–296 (October 1989). For example, compounds may be contacted with a cell which expresses the receptor polypeptide of the present invention and a second messenger response, e.g., signal transduction or pH chances, may be measured to determine whether the potential compound activates or inhibits the receptor.

Another such screening technique involves introducing RNA encoding the receptor into Xenopus oocytes to transiently express the receptor. The receptor oocytes may then be contacted with the receptor ligand and a compound to be screened, followed by detection of inhibition or activation of a calcium signal in the case of screening for compounds which are thought to inhibit activation of the receptor.

Another screening technique involves expressing in cells a construct wherein the receptor is linked to a phospholipase C or D. Such cells include endothelial cells, smooth muscle cells, embryonic kidney cells, etc. The screening may be accomplished as hereinabove described by detecting activation of the receptor or inhibition of activation of the receptor from the phospholipase signal.

Another method involves screening for compounds which inhibit activation of the receptor polypeptide of the present invention antagonists by determining inhibition of binding of labeled ligand to cells which have the receptor on the surface thereof. Such a method involves transfecting a eukaryotic cell with DNA encoding the receptor such that the cell expresses the receptor on its surface and contacting the cell with a compound in the presence of a labeled form of a known ligand. The ligand can be labeled, e.g., by radioactivity. The amount of labeled ligand bound to the receptors is measured, e.g., by measuring radioactivity of the receptors. If the compound binds to the receptor as determined by a reduction of labeled ligand which binds to the receptors, the binding of labeled ligand to the receptor is inhibited.

Further screening assays for agonist and antagonist of the present invention are described in Tartaglia, L. A., and Goeddel, D. V., *J. Biol. Chem.* 267(7):4304–4307(1992).

Thus, in a further aspect, a screening method is provided for determining whether a candidate agonist or antagonist is capable of enhancing or inhibiting a cellular response to a TNF-family ligand. The method involves contacting cells which express the DR4 polypeptide with a candidate compound and a TNF-family ligand, assaying a cellular response, and comparing the cellular response to, a standard cellular response, the standard being assayed when contact is made with the ligand in absence of the candidate compound, whereby an increased cellular response over the standard indicates that the candidate compound is an agonist of the ligand/receptor signaling pathway and a decreased cellular response compared to the standard indicates that the candidate compound is an antagonist of the ligand/receptor signaling pathway. By "assaying a cellular response" is intended qualitatively or quantitatively measuring a cellular response to a candidate compound and/or a TNF-family ligand (e.g., determining or estimating an increase or decrease in T cell proliferation or tritiated thymidine labeling). By the invention, a cell expressing the DR4 polypeptide can be contacted with either an endogenous or exogenously administered TNF-family ligand.

Agonist according to the present invention include naturally occurring and synthetic compounds such as, for example, TNF family ligand peptide fragments, transforming growth factor, neurotransmitters (such as glutamate, dopamine, N-methyl-D-aspartate), tumor suppressors (p53), cytolytic T cells and antimetabolites. Preferred agonist include chemotherapeutic drugs such as, for example, cisplatin, doxorubicin, bleomycin, cytosine arabinoside, nitrogen mustard, methotrexate and vincristine. Others include ethanol and -amyloid peptide. (*Science* 267:1457–1458 (1995)). Further preferred agonist include polyclonal and monoclonal antibodies raised against the DR4 polypeptide, or a fragment thereof. Such agonist antibodies raised against a TNF-family receptor are disclosed in Tartaglia, L. A., et al., *Proc. Natl. Acad. Sci. USA* 88:9292–9296 (1991); and Tartaglia, L. A., and Goeddel, D. V., *J. Biol. Chem.* 267 (7):4304–4307 (1992) See, also, PCT Application WO 94/09137.

Antagonist according to the present invention include naturally occurring and synthetic compounds such as, for example, the CD40 ligand, neutral amino acids, zinc, estrogen, androgens, viral genes (such as Adenovirus E1B, Baculovirus p35 and IAP, Cowpox virus crmA, Epstein-Barr virus BHRF1. LMP-1, African swine fever virus LMW5-HL, and Herpesvirus ICP 34.5), calpain inhibitors, cysteine protease inhibitors, and tumor promoters (such as PMA, Phenobarbital, and hexachlorocyclohexanes (e.g., $\alpha$-,$\beta$-, or $\gamma$-hexachlorocyclohexane).

Other potential antagonists include antisense molecules. Antisense technology can be used to control gene expression through antisense DNA or RNA or through triple-helix formation. Antisense techniques are discussed, for example, in Okano, *J. Neurochem.* 56:560 (1991); *Oligodeoxynucleotides as Antisense Inhibitors of Gene Expression*, CRC Press, Boca Raton, Fla. (1988). Triple helix formation is discussed in, for instance Lee et al., *Nucleic Acids Research* 6:3073 (1979); Cooney et al., *Science* 241:456 (1988); and Dervan et al., *Science* 251:1360 (1991). The methods are based on binding of a polynucleotide to a complementary DNA or RNA.

For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of the receptor. The antisense RNA oligonucleotide hybridizes to the mRNA in vivo and blocks translation of the mRNA molecule into receptor polypeptide. The oligonucleotides described above can also be delivered to cells such that the antisense RNA or DNA may be expressed in vivo to inhibit production of the receptor.

Further antagonist according to the present invention include soluble forms of DR4, i.e.,DR4 fragments that include the ligand binding domain from the extracellular region of the full length receptor. Such soluble forms of the receptor, which may be naturally occurring or synthetic, antagonize DR4 mediated signaling by competing with the cell surface DR4 for binding to TNF-family ligands. Thus, soluble forms of the receptor that include the ligand binding domain are novel cytokines capable of inhibiting apoptosis induced by TNF-family ligands. These are preferably expressed as dimers or trimers, since these have been shown to be superior to monomeric forms of soluble receptor as antagonists, e.g., IgGFc-TNF receptor family fusions. Other such cytokines are known in the art and include Fas B (a soluble form of the mouse Fas receptor) that acts physiologically to limit apoptosis induced by Fas ligand (Hughes, D. P. and Crispe, I. N., *J. Exp. Med.* 182:1395–1401 (1995)).

The experiments set forth in Example 5 demonstrates that DR4 is a death domain-containing molecule capable of triggering apoptosis which is important in the regulation of the immune system. In addition, the experiments set forth below demonstrate that DR4-induced apoptosis was blocked by the inhibitors of ICE-like proteases, CrmA and z-VAD-fmk. Thus, inhibitors of ICE-like proteases, FADD-DN and FLICE-DN/MACHalC360S could also be used as antagonists for DR4 activity.

The term "antibody" (Ab) or "monoclonal antibody" (mAb) as used herein is meant to include intact molecules as well as fragments thereof (such as, for example, Fab and F(ab')$_2$ fragments) which are capable of binding an antigen. Fab and F (ab')$_2$ fragments lack the Fc fragment of intact antibody, clear more rapidly from the circulation, and may have less non-specific tissue binding of an intact antibody (Wahl et al., *J. Nucl. Med.* 24:316–325 (1983)).

Antibodies according to the present invention may be prepared by any of a variety of methods using DR4 immunogens of the present invention. As indicated, such DR4 immunogens include the full length DR4 polypeptide (which may or may not include the leader sequence) and DR4 polypeptide fragments such as the ligand binding domain, the transmembrane domain, the intracellular domain and the death domain.

Proteins and other compounds which bind the DR4 domains are also candidate agonist and antagonist according to the present invention. Such binding compounds can be "captured" using the yeast two-hybrid system (Fields and Song, *Nature* 340:245–246 (1989)). A modified version of the yeast two-hybrid system has been described by Roger Brent and his colleagues (Gyuris, J. et al., *Cell* 75:791–803 (1993); Zervos, A. S. et al., *Cell* 72:223–232 (1993)). Preferably, the yeast two-hybrid system is used according to the present invention to capture compounds which bind to either the DR4 ligand binding domain or to the DR4 intracellular domain. Such compounds are good candidate agonist and antagonist of the present invention.

By a "TNF-family ligand" is intended naturally occurring, recombinant, and synthetic ligands that are capable of binding to a member of the TNF receptor family and inducing and/or blocking the ligand/receptor signaling pathway. Members of the TNF ligand family include, but are not limited to, DR4 ligands, TRAIL, TNF-$\alpha$, TNF- $\beta$-$\alpha$, lymphotoxin-$\alpha$ (LT-$\alpha$, also known as TNF-$\beta$), LT-$\beta$ (found in complex heterotrimer LT-$\alpha$2-$\beta$), FasL, VEGI (International Publication No. WO 96/14328), AIM-I (International Publication No. WO 97/33899), AIM-II (International Publication No. WO 97/34911), APRIL (J. Exp. Med. 188(6):1185–1190), endokine-alpha (International Publication No. WO 98/07880), neutrokine-alpha (International Publication No. WO 98/18921), CD40L, CD27L, CD30L, 4-1BBL, OX40L and nerve growth factor (NGF).

Representative therapeutic applications of the present invention are discussed in-more detail below. The state of immunodeficiency that defines AIDS is secondary to a decrease in the number and function of CD4$^+$ T-lymphocytes. Recent reports estimate the daily loss of CD4$^+$ T cells to be between $3.5 \times 10^7$ and $2 \times 10^9$ cells (Wei X., et al., Nature 373:117–122 (1995)). One cause of CD4$^+$ T cell depletion in the setting of HIV infection is believed to be HIV-induced apoptosis. Indeed, HIV-induced apoptotic cell death has been demonstrated not only in vitro but also, more importantly, in infected individuals (Ameisen, J. C., AIDS 8:1197–1213 (1994); Finkel, T. H., and Banda, N. K., Curr. Opin. Immunol 6:605–615(1995); Muro-Cacho, C. A. et al., J. Immunol. 154:5555–5566 (1995)). Furthermore, apoptosis and CD4$^+$ T-lymphocyte depletion is tightly correlated in different animal models of AIDS (Brunner, T., et al., Nature 373:441–444 (1995); Gougeon, M. L., et al., AIDS Res. Hum. Retroviruses 9:553–563 (1993)) and, apoptosis is not observed in those animal models in which viral replication does not result in AIDS (Gougeon, M. L. et al., AIDS Res. Hum. Retroviruses 9:553–563 (1993)). Further data indicates that uninfected but primed or activated T lymphocytes from HIV-infected individuals undergo apoptosis after encountering the TNF-family ligand FasL. Using monocytic cell lines that result in death following HIV infection, it has been demonstrated that infection of U937 cells with HIV results in the de novo expression of FasL and that FasL mediates HIV-induced apoptosis (Badley, A. D. et al., J. Virol. 70:199–206 (1996)). Further the TNF-family ligand was detectable in uninfected macrophages and its expression was upregulated following HIV infection resulting in selective killing of uninfected CD4 T-lymphocytes (Badley, A. D et al., J. Virol 70:199–206 (1996)). Thus, by the invention, a method for treating HIV$^+$ individuals is provided which involves administering an antagonist of the present invention to reduce selective killing of CD4 T-lymphocytes. Modes of administration and dosages are discussed in detail below.

In rejection of an allograft, the immune system of the recipient animal has not previously been primed to respond because the immune system for the most part is only primed by environmental antigens. Tissues from other members of the same species have not been presented in the same way that, for example, viruses and bacteria have been presented. In the case of allograft rejection, immunosuppressive regimens are designed to prevent the immune system from reaching the effector stage. However, the immune profile of xenograft rejection may resemble disease recurrence more that allograft rejection. In the case of disease recurrence, the immune system has already been activated, as evidenced by destruction of the native islet cells. Therefore, in disease recurrence the immune system is already at the effector stage. Agonist of the present invention are able to suppress the immune response to both allografts and xenografts because lymphocytes activated and differentiated into effector cells will express the DR4 polypeptide, and thereby are susceptible to compounds which enhance apoptosis. Thus, the present invention further provides a method for creating immune privileged tissues. Antagonist of the invention can further be used in the treatment of Inflammatory Bowel-Disease.

DR4 antagonists may be useful for treating inflammatory diseases, such as rheumatoid arthritis, osteoarthritis, psoriasis, septicemia, and inflammatory bowel disease.

In addition, due to lymphoblast expression of DR4, soluble DR4, agonist or antagonist mABs may be used to treat this form of cancer. Further, soluble DR4 or neutralizing mABs may be used to treat various chronic and acute forms of inflammation such as rheumatoid arthritis, osteoarthritis, psoriasis, septicemia, and inflammatory bowel disease.

Modes of Administration

The agonist or antagonists described herein can be administered in vitro, ex vivo, or in vivo to cells which express the receptor of the present invention. By administration of an "effective amount" of an agonist or antagonist is intended an amount of the compound that is sufficient to enhance or inhibit a cellular response to a TNF-family ligand and include polypeptides. In particular, by administration of an "effective amount" of an agonist or antagonists is intended an amount effective to enhance or inhibit DR4 mediated apoptosis. Of course, where apoptosis is to be enhanced, an agonist according to the present invention can be co-administered with a TNF-family ligand. One of ordinary skill will appreciate that effective amounts of an agonist or antagonist can be determined empirically and may be employed in pure form or in pharmaceutically acceptable salt, ester or prodrug form The agonist or antagonist may be administered in compositions in combination with one or more pharmaceutically acceptable excipients.

It will be understood that, when administered to a human patient, the total daily usage of the compounds and compositions of the present invention will be decided by the attending physician within the scope of sound medical judgement. The specific therapeutically effective dose level for any particular patient will depend upon factors well known in the medical arts.

As a general proposition, the total pharmaceutically effective amount of DR4 polypeptide administered parenterally per dose will be in the range of about 1 μg/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the DR4 agonists or antagonists is typically administered at a dose rate of about 1 μg/kg/hour to about 50 μg/kg/hour, either by 1–4 injections per day or by continuous subcutaneous infusions, for example, using a mini-pump. An intravenous bag solution may also be employed.

Dosaging may also be arranged in a patient specific manner to provide a predetermined concentration of an agonist or antagonist in the blood, as determined by the RIA technique. Thus patient dosaging may be adjusted to achieve regular on-going trough blood levels, as measured by RIA, on the order of from 50 to 1000 ng/ml, preferably 150 to 500 ng/ml.

Pharmaceutical compositions are provided comprising an agonist or antagonist and a pharmaceutically acceptable carrier or excipient, which may be administered orally, rectally, parenterally, intracisternally, intravaginally, intraperitoneally, topically (as by powders, ointments, drops or transdermal patch), bucally, or as an oral or nasal spray. Importantly, by co-administering an agonist and a TNF-family ligand, clinical side effects can be reduced by using lower doses of both the ligand and the agonist. It will be understood that the agonist can be "co-administered" either before, after, or simultaneously with the TNF-family ligand, depending on the exigencies of a particular therapeutic application. By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

Pharmaceutical compositions of the present invention for parenteral injection can comprise pharmaceutically acceptable sterile aqueous or nonaqueous solutions, dispersions, suspensions or emulsions as well as sterile powders for reconstitution into sterile injectable solutions or dispersions just prior to use.

In addition to soluble DR4 polypeptides, DR4 polypeptide containing the transmembrane region can also be used when appropriately solubilized by including detergents, such as CHAPS or NP40, with buffer.

EXAMPLE 1

Expression and Purification in E. coli

The DNA sequence encoding the mature DR4 protein in the deposited cDNA clone (ATCC No. 97853) is amplified using PCR oligonucleotide primers specific to the amino terminal sequences of the DR4 protein and to vector sequences 3' to the gene. Additional nucleotides containing restriction sites to facilitate cloning are added to the 5' and 3' sequences respectively.

The following primers are used for expression of DR4 extracellular domain in E. coli 5' primer 5'-GCGGCATGCATGATCAATCAATTGGCAC-3' (SEQ ID NO:8) contains the underlined SphI site. 3' primer: 5'-GCGAAGCTTTCAATTATGTCCATTGCCTG-3' (SEQ ID NO:12) contains the underlined HindIII site. Vector is pQE60.

The restriction sites are convenient to restriction enzyme sites in the bacterial expression vector pQE60, which are used for bacterial expression in these examples. (Qiagen, Inc. 9259 Eton Avenue, Chatsworth, Calif., 91311). pQE60 encodes ampicillin antibiotic resistance ("Amp"") and contains a bacterial origin of replication ("ori"), an IPTG inducible promoter, a ribosome binding site ("RBS").

The amplified DR4 DNA and the vector pQE60 both are digested with SphI and HindIII and the digested DNAs are then ligated together. Insertion of the DDCR protein DNA into the restricted pQE60 vector places the DR4 protein coding region downstream of and operably linked to the vector's IPTG-inducible promoter and in-frame with an initiating AUG appropriately positioned for translation of DR4 protein.

The ligation mixture is transformed into competent E. coli cells using standard procedures. Such procedures are described in Sambrook et al., Molecular Cloning: a Laboratory Manual, 2nd Ed.; Cold Spring Harbor Laboratory Press, Cold Spring Harbor, N.Y. (1989). E. coli strain M15/rep4, containing multiple copies of the plasmid pREP4, which expresses lac repressor and confers kanamycin resistance ("Kan"), is used in carrying out the illustrative example described herein. This strain, which is only one of many that are suitable for expressing DR4 protein, is available commercially from Qiagen.

Transformants are identified by their ability to grow on LB plates in the presence of ampicillin and kanamycin. Plasmid DNA is isolated from resistant colonies and the identity of the cloned DNA confirmed by restriction analysis.

Clones containing the desired constructs are grown overnight ("O/N") in liquid culture in LB media supplemented with both ampicillin (100 μg/ml) and kanamycin (25 μg/ml).

The O/N culture is used to inoculate a large culture, at a dilution of approximately 1:100 to 1:250. The cells are grown to an optical density at 600 nm ("OD600") of between 0.4 and 0.6. Isopropyl-B-D-thiogalactopyranoside ("IPTG") is then added to a final concentration of 1 mM to induce transcription from lac repressor sensitive promoters, by inactivating the lacI repressor. Cells subsequently are incubated further for 3 to 4 hours. Cells then are harvested by centrifugation and disrupted, by standard methods. Inclusion bodies are purified from the disrupted cells using routine collection techniques, and protein is solubilized from the inclusion bodies into 8M urea. The 8M urea solution containing the solubilized protein is passed over a PD-10 column in 2× phosphate-buffered saline ("PBS"), thereby removing the urea, exchanging the buffer and refolding the protein. The protein is purified by a further step of chromatography to remove endotoxin. Then, it is sterile filtered. The sterile filtered protein preparation is stored in 2× PBS at a concentration of 95 μ/ml.

EXAMPLE 2

Expression in Mammalian Cells

Most of the vectors used for the transient expression of a given gene sequence in mammalian cells carry the SV40 origin of replication. This allows the replication of the vector to high copy numbers in cells (e.g. COS cells) which express the T antigen required for the initiation of viral DNA synthesis. Any other mammalian cell line can also be utilized for this purpose.

A typical mammalian expression vector contains the promoter element, which mediates the initiation of transcription of mRNA, the protein coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRs) from Retroviruses, eg. RSV, HTLVI, HIVI and the early promoter of the cytomegalovirus (CMV). However, also cellular signals can be used (e.g., human actin, promoter). Suitable expression vectors for use in practicing the present invention include, for example, vectors such as pSVL and pMSG (Pharmacia, Uppsala, Sweden), pRSVcat (ATCC 37152), pSV2dhfr (ATCC 37146) and pBC12M1 (ATCC67109). Mammalian host cells that could be used include, human HeLa, 283, H9 and Jurkat cells, mouse NIH3T3 and C127 cells, Cos 1, Cos 7 and CV1 African green monkey cells, quail QC1–3 cells, mouse L cells and Chinese hamster ovary cells.

Alternatively, a gene of interest can be expressed in stable cell lines that contain the gene integrated into a chromosome. The co-transfection with a selectable marker such as dhfr, gpt, neomycin, hygromycin allows the identification and isolation of the transfected cells.

The transfected gene can also be amplified to express large amounts of the encoded protein. The DHFR (dihydrofolate reductase) is a useful marker to develop cell lines that carry several hundred or even several thousand copies of the gene of interest. Using this marker, the mammalian cells are grown in increasing amounts of methotrexate for selection and the cells with the highest resistance are selected. These cell lines contain the amplified gene(s) integrated into a chromosome Chinese hamster ovary (CHO) cells are often used for the production of proteins.

The expression vectors pC1 and pC4 contain the strong promoter (LTR) of the Rous Sarcoma Virus (Cullen et al., *Molecular and Cellular Biology* 438:44701 (March 1985)), plus a fragment of the CMV-enhancer (Boshart et al., *Cell* 41:521–530 (1985)). Multiple cloning sites, e.g. with the restriction enzyme cleavage sites BamHI, XbaI and Asp718, facilitate the cloning of the gene of interest. The vectors contain in addition the 3' intron, the polyadenylation and termination signal of the rat preproinsulin gene.

Cloning and Expression in CHO Cells

The vector pC4 is used for the expression of DR4 polypeptide. Plasmid pC4 is a derivative of the plasmid pSV2-dhfr (ATCC Accession No. 37146). The plasmid contains the mouse DHFR gene under control of the SV40 early promoter. Chinese hamster ovary- or other cells lacking dihydrofolate activity that are transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented (see, e.g., Alt, F. W., Kellems, R. M., Bertino, J. R., and Schimke, R. T., 1978, *J. Biol. Chem.* 253:1357–1370, Hamlin, J. L. and Ma, C. 1990, *Biochem. et Biophys. Acta,* 1097:107–143, Page, M. J. and Sydenham, M. A. 1991, *Biotechnology* 9:64–68). Cells grown in increasing concentrations of MTX develop resistance to the drug by overproducing the target enzyme, DHFR, as a result of amplification of the DHFR gene. If a second gene is linked to the DHFR gene, it is usually co-amplified and over-expressed. It is known in the art that this approach may be used to develop cell lines carrying more than 1,000 copies of the amplified gene(s). Subsequently, when the methotrexate is withdrawn, cell lines are obtained which contain the amplified gene integrated into one or more chromosome(s) of the host cell.

Plasmid pC4 contains for expressing the gene of interest the strong promoter of the long terminal repeat (LTR) of the Rouse Sarcoma Virus (Cullen, et al., *Molecular and Cellular Biology*, March 1985:438–447) plus a fragment isolated from the enhancer of the immediate early gene of human cytomegalovirus (CMV) (Boshart et al., *Cell* 41:521–530 (1985)). Downstream of the promoter are the following single restriction enzyme cleavage sites that allow the integration of the genes: BamHI, Xba I, and Asp718. Behind these cloning sites the plasmid contains the 3' intron and polyadenylation site of the rat preproinsulin gene. Other high efficiency promoters can also be used for the expression, e.g., the human β-actin promoter, the SV40 early or late promoters or the long terminal repeats from other retroviruses, e.g., HIV and HTLVI. Clontech's Tet-Off and Tet-On gene expression systems and similar systems can be used to express the DR4 polypeptide in a regulated way in mammalian cells (Gossen, M., & Bujard, H. 1992, *Proc. Natl. Acad. Sci. USA* 89:5547–5551). For the polyadenylation of the mRNA other signals, e.g., from the human growth hormone or globin genes can be used as well. Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC4 is digested with the restriction enzyme BamHI and then dephosphorylated using calf intestinal phosphates by procedures known in the art. The vector is then isolated from a 1% agarose gel.

The DNA sequence encoding the complete polypeptide is amplified using PCR oligonucleotide primers corresponding to the 5' and 3' sequences of the desired portion of the gene. The 5' primer containing the underlined BamHI site, a Kozak sequence, and an AUG start codon, has the following sequence:

5' GCGGGATCCGCCATCATGGCGCCACCAC-CAGCTAGA 3' (SEQ ID NO:9). The 3' primer, containing the underlined BamHI site, has the following sequence:

5' GCGGGATCCTCACTCCAAGGACACGGCAGAGCC 3' (SEQ ID NO:10).

The amplified fragment is digested with the endonuclease BamHI and then purified again on a 1% agarose gel. The isolated fragment and the dephosphorylated vector are then ligated with T4 DNA ligase. *E. coli* HB 101 or XL-1 Blue cells are then transformed and bacteria are identified that contain the fragment inserted into plasmid pC4 using, for instance, restriction enzyme analysis.

Chinese hamster ovary cells lacking an active DHFR gene are used for transfection. Five µg of the expression plasmid pC4 is cotransfected with 0.5 µg of the plasmid pSVneo using lipofectin (Felgner et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of metothrexate plus 1 mg/ml G418 After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 µM, 2 µM, 5 µM, 10 mM, 20 mM). The same procedure is repeated until clones are obtained which grow at a concentration of 100–200 µM. Expression of the desired gene product is analyzed, for instance, by SDS-PAGE and Western blot or by reversed phase HPLC analysis.

EXAMPLE 3

Cloning and Expression of the Soluble Extracellular Domain of DR4 in a Baculovirus Expression System The cDNA sequence encoding the soluble extracellular domain of DR4 protein in the deposited clone (ATCC No. 97853) is amplified using PCR oligonucleotide primers corresponding to the 5' and 3' sequences of the gene:

The 5' primer for DR4 has the sequence

5' GCGGGATCCGCCATCATGGCGCCACCAC-CAGCTAGA 3' (SEQ ID NO:9) containing the underlined BamHI restriction enzyme site. Inserted into an expression vector, as described below, the 5' end of the amplified fragment encoding DR4 provides an efficient cleavage signal peptide. An efficient signal for initiation of translation in eukaryotic cells, as described by Kozak, M., *J. Mol. Biol.* 196:947–950 (1987) is appropriately located in the vector portion of the construct.

The 3' primer for both DR4 has the sequence 5' GCGG-GATCCTCAATTATGTCCATTGCCTG 3' (SEQ ID NO:11) containing the underlined BamHI restriction followed by nucleotides complementary to the DR4 nucleotide sequence set out in FIG. 1, followed by the stop codon.

The amplified fragment is isolated from a 1% agarose gel using a commercially available kit ("Geneclean, " BIO 101 Inc., La Jolla, Calif.) The fragment then is digested with BamHI and Asp718 and again is purified on a 1% agarose gel.

The vector pA2 is used to express the DR4 protein in the baculovirus expression system, using standard methods, such as those described in Summers et al., *A Manual of Methods for Baculovirus Vectors and Insect Cell Culture Procedures*, Texas Agricultural Experimental Station Bulletin No. 1555 (1987). This expression vector contains the strong polyhedron promoter of the Autograph californica nuclear polyhedrosis virus (ACMNPV) followed by convenient restriction sites. For an easy selection of recombinant virus the beta-galactosidase gene from *E. coli* is inserted in the same orientation as the polyhedron promoter and is followed by the polyadenylation signal of the polyhedron gene. The polyhedron sequences are flanked at both sides by viral sequences for cell-mediated homologous recombination with wild-type viral DNA to generate viable virus that express the cloned polynucleotide.

Many other baculovirus vectors could be used in place of pA2, such as pAc373, pVL941 and pAcIM1 provided, as those of skill readily will appreciate, that construction provides appropriately located signals for transcription, translation, trafficking and the like, such as an in-frame AUG and a signal peptide, as required. Such vectors are described in Luckow et al., *Virology* 170:31–39, among others.

The plasmid is digested with the restriction enzyme Barn HI and then is dephosphorylated using calf intestinal phosphatase, using routine procedures known in the art. The DNA is then isolated from a 1% agarose gel using a commercially available kit ("Geneclean" BIO 101 Inc., La Jolla, Calif.).

Fragment and the dephosphorylated plasmid are ligated together with T4 DNA ligase. *E. coli* HB101 cells are transformed with ligation mix and spread on culture plates. Bacteria are identified that contain the plasmid with the human DDCR gene by digesting DNA from individual colonies using BamHI and then analyzing the digestion product by gel electrophoresis. The sequence of the cloned fragment is confirmed by DNA sequencing. This plasmid is designated herein pBac DR4.

5 µg of the plasmid pBac DR4 is co-transfected with 1.0 µg of a commercially available linearized baculovirus DNA ("BaculoGold™ baculovirus DNA", Pharmingen, San Diego, Calif.), using the lipofection method described by Felgner et al., *Proc. Natl. Acad. Sci. USA* 84:7413–7417 (1987). 1 µg of BaculoGold™ virus DNA and 5 µg of the plasmid pBac DR4 are mixed in a sterile well of a microliter plate containing 50 µl of serum free Grace's medium (Life Technologies Inc., Gaithersburg, Md.). Afterwards 10 µl Lipofectin plus 90 µl Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is rocked back and forth to mix the newly added solution. The plate is then incubated for 5 hours at 27 C. After 5 hours the transfection solution is removed from the plate and 1 ml of Grace's insect medium supplemented with 10% fetal calf serum is added. The plate is put back into an incubator and cultivation is continued at 27 C. for four days.

After four days the supernatant is collected and a plaque assay is performed, as described by Summers and Smith, cited above. An agarose gel with "Blue Gal"(Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10).

Four days after serial dilution, the virus is added to the cells. After appropriate incubation, blue stained plaques are picked with the tip of an Eppendorf pipette. The agar containing the recombinant viruses is then resuspended in an Eppendorf tube containing 200 µl of Grace's medium. The agar is removed by a brief centrifugation and the supernatant containing the recombinant baculovirus is used to infect Sf9 cells seeded in 35 mm dishes. Four days later the supernatants of these culture dishes are harvested and then they are stored at 4 C. A clone containing properly inserted DR4 is identified by DNA analysis including restriction mapping and sequencing. This is designated herein as V-DR4.

Sf9 cells are grown in Grace's medium supplemented with 10% heat-inactivated FBS. The cells are infected with the recombinant baculovirus V- DR4 at a multiplicity of infection ("MOI") of about 2 (about 1 to about 3). Six hours later the medium is removed and is replaced with SF900 II medium minus methionine and cysteine (available from Life Technologies Inc., Gaithersburg). 42 hours later, 5 gCi of $^{35}$-methionine and 5 µCi $^{35}$S cysteine (available from Amersham) are added. The cells are further incubated for 16 hours and then they are harvested by centrifugation, lysed and the labeled proteins are visualized by SDS-PAGE and autoradiography.

EXAMPLE 4

Tissue Distribution of DR4 Gene Expression

Northern blot analysis is carried out to examine DR4 gene (ATCC No. 97853) expression in human tissues, using methods described by, among others, Sambrook et al., cited above. A cDNA probe containing the entire nucleotide sequence of the DR4 protein (SEQ ID NO:1) is labeled with $^{32}$P using the rediprime™ DNA labeling system (Amersham Life Science), according to manufacturer's instructions. After labeling, the probe is purified using a CHROMA SPIN-100™ column (Clontech Laboratories, Inc.), according to manufacturer's protocol number PT1200–1. The purified labeled probe is then used to examine various human tissues for DR4 mRNA.

Multiple Tissue Northern (MTN) blots containing various human tissues (H) or human immune system tissues (IM) are obtained from Clontech and are examined with labeled probe using ExpressHyb™ hybridization solution (Clontech) according to manufacturer's protocol number PT 1190–1. Following hybridization and washing, the blots are mounted and exposed to film at −70 C overnight, and films developed according to standard procedures Expression of DR4 was detected in tissues enriched in lymphocytes including amniotic cells, heart, liver cancer, kidney, peripheral blood leukocytes, activated T-cell, K562 plus PMA, W138 cells, Th2 cells, human tonsils, and CD34 depleted buffy coat (cord blood). It can be envisaged that DR4 plays a role in lymphocyte homeostasis.

EXAMPLE 5

DR4 Induced Apoptosis

Overexpression of Fas/APO-1 and TNFR-1 in mammalian cells mimics receptor activation (M. Muzio, et al., *Cell*

85, 817–827 (1996); M. P. Boldin, et al., *Cell* 85, 803–815 (1996)). Thus, this system was utilized to study the functional role of DR4. Transient expression of DR4 in MCF7 human breast carcinoma cells and 293 human embryonic kidney cells induced rapid apoptosis.

Cell death assays are performed essentially as previously described (A. M. Chinnaiyan, et al., *Cell* 81, 505–12 (1995); M. P. Boldin, et al., *J Biol Chem* 270, 7795–8 (1995); F. C. Kischkel, et al., *EMBO* 14, 5579–5588 (1995); A. M. Chinnaiyan, et al., *J Biol Chem* 271, 4961–4965 (1996)). Briefly, MCF-7 human breast carcinoma clonal cell lines stably transfected with either vector alone or a CmA expression construct (M. Tewari, et al., i J Biol Chem 270, 3255–60 (1995)), are transiently transfected with pCMV-DR4-galatosidase (or pCMV-DR4-galactosidase (lacking the death domain)) in the presence of a ten-fold excess of pcDNA3 expression constructs encoding the indicated proteins using lipofectamine (GIBCO-BRL). 293 cells are likewise transfected using the $CaPO_4$ method. The ICE family inhibitor z-VAD-fmk (Enzyme Systems Products, Dublin, Calif.) is added to the cells at a concentration of 10 $\mu$M, 5 hrs after transfection. 32 hours following transfection, cells are fixed and stained with X-Gal as previously described (A. M. Chinnaiyan, et al., *Cell* 81, 505–12 (1995); M. P. Boldin, et al., *J Biol Chem* 270, 7795–8 (1995); F. C. Kischkel, et al., *EMBO* 14, 5579–5588 (1995)).

The cells displayed morphological alterations typical of cells undergoing apoptosis, becoming rounded, condensed and detaching from the dish. Similar to TNFR-1 and Fas/APO-1 (M. Muzio, et al., *Cell* 85,817–827 (1996); M. P. Boldin, et al., *Cell* 85, 803–815 (1996); M. Tewari, et al., *J Biol Chem* 270, 3255–60 (1995)), DR4-induced apoptosis was blocked by the inhibitors of ICE-like proteases, CmA and z-VAD-fmk It will be clear that the invention may be practiced otherwise than as particularly described in the foregoing description and examples.

Numerous modifications and variations of the present invention are possible in light of the above teachings and, therefore, are within the scope of the appended claims.

The entire disclosures of all patents, patent applications, and publications referred to herein are hereby incorporated by reference.

What is claimed is:

1. An isolated agonist antibody or fragment thereof that specifically binds to a polypeptide consisting of amino acids 24 to 238 of SEQ ID NO:2, wherein said antibody or fragment thereof enhances the apoptotic activity of DR4.

2. The antibody or fragment thereof of claim 1, wherein the polypeptide is glycosylated.

3. The antibody or fragment thereof of claim 1, wherein said antibody or fragment thereof is polyclonal.

4. The antibody or fragment thereof of claim 1, wherein said antibody or fragment thereof is monoclonal.

5. The antibody or fragment thereof of claim 1, wherein said antibody or fragment thereof is selected from the group consisting of:
   (a) a chimeric antibody or fragment thereof;
   (b) a Fab fragment; and
   (c) a F(ab')$_2$ fragment.

6. The antibody or fragment thereof of claim 1, wherein said antibody or fragment thereof is labeled.

7. The antibody or fragment thereof of claim 6, wherein said label is selected from the group consisting of:

(a) an enzyme,
   (b) a fluorescent label; and
   (c) a radioisotope.

8. The antibody or fragment thereof of claim 1, wherein said antibody or fragment thereof specifically binds to said polypeptide in a Western blot.

9. The antibody or fragment thereof of claim 1, wherein said antibody or fragment thereof specifically binds to said polypeptide in an ELISA.

10. An isolated cell that produces the antibody or fragment thereof of claim 1.

11. A hybridoma that produces the antibody or fragment thereof of claim 1.

12. A composition comprising the antibody or fragment thereof of claim 1, and a carrier.

13. A method of producing the antibody or fragment thereof of claim 1 comprising:
    (a) immunizing an animal with a polypeptide consisting of amino acids 24–468 of SEQ ID NO:2 or an epitope-bearing fragment thereof; and
    (b) recovering said antibody or fragment thereof.

14. An isolated agonist antibody or fragment thereof which specifically binds to DR4 polypeptide expressed on the surface of a cell, wherein said cell DR4 polypeptide is encoded by a polynucleotide encoding amino acids 1–468 of SEQ ID NO:2.

15. The antibody or fragment thereof of claim 14, wherein the polypeptide is glycosylated.

16. The antibody or fragment thereof of claim 14, wherein said antibody or fragment thereof is polyclonal.

17. The antibody or fragment thereof of claim 14, wherein said antibody or fragment thereof is monoclonal.

18. The antibody or fragment thereof of claim 14, wherein said antibody or fragment thereof is selected from the group consisting of:
    (a) a chimeric antibody or fragment thereof;
    (b) a Fab fragment; and
    (c) a F(ab')$_2$ fragment.

19. The antibody or fragment thereof of claim 14, wherein said antibody or fragment thereof is labeled.

20. The antibody or fragment thereof of claim 19, wherein said label is selected from the group consisting of:
    (a) an enzyme;
    (b) a fluorescent label; and
    (c) a radioisotope.

21. The antibody or fragment thereof of claim 14, wherein said antibody or fragment thereof specifically binds to said polypeptide in a Western blot.

22. The antibody or fragment thereof of claim 14, wherein said antibody or fragment thereof specifically binds to said polypeptide in an ELISA.

23. An isolated cell that produces the antibody or fragment thereof of claim 14.

24. A hybridoma that produces the antibody or fragment thereof of claim 14.

25. A composition comprising the antibody or fragment thereof of claim 14, and a carrier.

26. A method of producing the antibody or fragment thereof of claim 14 comprising:
    (a) immunizing an animal with a polypeptide consisting of amino acids 24–468 of SEQ ID NO:2 or an epitope-bearing fragment thereof; and
    (b) recovering said antibody or fragment thereof.

27. An isolated agonist antibody or fragment thereof that specifically binds the extracellular domain of the polypeptide encoded by the cDNA clone contained in ATCC Deposit No. 97853.

28. The antibody or fragment thereof of claim 27, wherein the polypeptide is glycosylated.

29. The antibody or fragment thereof of claim 27, wherein said antibody or fragment thereof is polyclonal.

30. The antibody or fragment thereof of claim 27, wherein said antibody or fragment thereof is monoclonal.

31. The antibody or fragment thereof of claim 27, wherein said antibody or fragment thereof is selected from the group consisting of:
    (a) a chimeric antibody or fragment thereof;
    (b) a Fab fragment; and
    (c) a F(ab')$_2$ fragment.

32. The antibody or fragment thereof of claim 27, wherein said antibody or fragment thereof is labeled.

33. The antibody or fragment thereof of claim 27, wherein said label is selected from the group consisting of:
    (a) an enzyme;
    (b) a fluorescent label; and
    (c) a radioisotope.

34. The antibody or fragment thereof of claim 27, wherein said antibody or fragment thereof specifically binds to said polypeptide in a Western blot.

35. The antibody or fragment thereof of claim 27, wherein said antibody or fragment thereof specifically binds to said polypeptide in an ELISA.

36. An isolated cell that produces the antibody or fragment thereof of claim 27.

37. A hybridoma that produces the antibody or fragment thereof of claim 27.

38. A composition comprising the antibody or fragment thereof of claim 27, and a carrier.

39. A method of producing the antibody or fragment thereof of claim 27 comprising:
    (a) immunizing an animal with the polypeptide encoded by the cDNA clone contained in ATCC Deposit No. 97853 or an epitope hearing fragment thereof; and
    (b) recovering said antibody or fragment thereof.

40. An isolated agonist antibody or fragment thereof which specifically binds to DR4 polypeptide expressed on the surface of a cell, wherein said DR4 polypeptide is encoded by the cDNA contained in ATCC Deposit No. 97853.

41. The antibody or fragment thereof of claim 40, wherein the polypeptide is glycosylated.

42. The antibody or fragment thereof of claim 40, wherein said antibody or fragment thereof is polyclonal.

43. The antibody or fragment thereof of claim 40, wherein said antibody or fragment thereof is monoclonal.

44. The antibody or fragment thereof of claim 40, wherein said antibody or fragment thereof is selected from the group consisting of:
    (a) a chimeric antibody or fragment thereof;
    (b) a Fab fragment; and
    (c) a F(ab')$_2$ fragment.

45. The antibody or fragment thereof of claim 40, wherein said antibody or fragment thereof is labeled.

46. The antibody or fragment thereof of claim 45, wherein said label is selected from the group consisting of:
    (a) an enzyme;
    (b) a fluorescent label; and
    (c) a radioisotope.

47. The antibody or fragment thereof of claim 40, wherein said antibody or fragment thereof specifically binds to said polypeptide in a Western blot.

48. The antibody or fragment thereof of claim 40, wherein said antibody or fragment thereof specifically binds to said polypeptide in an ELISA.

49. An isolated cell that produces the antibody or fragment thereof of claim 40.

50. A hybridoma that produces the antibody or fragment thereof of claim 40.

51. A composition comprising the antibody or fragment thereof of claim 40, and a carrier.

52. A method of producing the antibody or fragment thereof of claim 40 comprising:
    (a) immunizing an animal with the polypeptide encoded by the cDNA clone contained in ATCC Deposit No. 97853 or epitope-bearing fragment thereof; and
    (b) recovering said antibody or fragment thereof.

* * * * *

UNITED STATES PATENT AND TRADEMARK OFFICE
CERTIFICATE OF CORRECTION

PATENT NO. : 6,943,020 B2
DATED : September 13, 2005
INVENTOR(S) : Ni et al.

It is certified that error appears in the above-identified patent and that said Letters Patent is hereby corrected as shown below:

Column 59,
Line 3, delete "cell" directly before "DR4 polypeptide".
Line 62, delete "claim 27" and replace with -- claim 32 --.

Signed and Sealed this

Twenty-fourth Day of January, 2006

JON W. DUDAS
*Director of the United States Patent and Trademark Office*